United States Patent
Segebrecht

(10) Patent No.: US 12,246,024 B2
(45) Date of Patent: Mar. 11, 2025

(54) COMPOSITIONS AND METHODS FOR CONTROLLING CERUMEN PRODUCTION

(71) Applicant: Free State Pharma Inc, Lawrence, KS (US)

(72) Inventor: Stephen L. Segebrecht, Lawrence, KS (US)

(73) Assignee: Free State Pharma Inc, Lawrence, KS (US)

( * ) Notice: Subject to any disclaimer, the term of this patent is extended or adjusted under 35 U.S.C. 154(b) by 105 days.

(21) Appl. No.: 16/713,303

(22) Filed: Dec. 13, 2019

(65) Prior Publication Data

US 2021/0177858 A1     Jun. 17, 2021

(51) Int. Cl.
| | |
|---|---|
| *A61K 31/5386* | (2006.01) |
| *A61K 9/00* | (2006.01) |
| *A61K 47/10* | (2017.01) |
| *A61P 27/16* | (2006.01) |

(52) U.S. Cl.
CPC .......... *A61K 31/5386* (2013.01); *A61K 47/10* (2013.01); *A61P 27/16* (2018.01); *A61K 9/0046* (2013.01)

(58) Field of Classification Search
CPC .... A61K 31/5386; A61K 9/0046; A61K 9/08; A61K 47/10; A61K 31/46; A61P 27/16
See application file for complete search history.

(56) References Cited

U.S. PATENT DOCUMENTS

| | | |
|---|---|---|
| 4,169,065 A | 9/1979 | Robertson |
| 4,769,171 A | 9/1988 | Harless |
| 4,895,875 A | 12/1990 | Winston |
| 5,238,933 A | 8/1993 | Catz et al. |
| 5,296,472 A | 3/1994 | Sanchez et al. |
| 5,380,711 A | 1/1995 | Sanchez et al. |
| 5,814,599 A | 9/1998 | Mitragotri et al. |
| 6,002,961 A | 12/1999 | Mitragotri et al. |
| 6,306,423 B1 | 10/2001 | Donovan et al. |
| 6,312,708 B1 | 11/2001 | Donovan |
| 6,417,179 B1 | 7/2002 | Burkhart et al. |
| 7,288,259 B2 | 10/2007 | Sanders et al. |
| 7,494,661 B2 | 2/2009 | Sanders |
| 7,494,979 B2 | 2/2009 | Currie et al. |
| 7,666,435 B2 | 2/2010 | Sanders et al. |
| 7,772,188 B2 | 8/2010 | Currie et al. |

(Continued)

FOREIGN PATENT DOCUMENTS

| | | | |
|---|---|---|---|
| WO | WO-2009068876 A1 * | 6/2009 | ............ A61P 17/10 |
| WO | 2019/126783 A1 | 6/2019 | |

OTHER PUBLICATIONS

Fullington, Douglas, et al.; "Evaluation of the safety and efficacy of a novel product for the removal of impacted human cerumen"; BMC Ear, Nose and Throat Disorders; 2017; 17:5; pp. 10.

(Continued)

*Primary Examiner* — Sarah Pihonak

(74) *Attorney, Agent, or Firm* — Polsinelli PC

(57) ABSTRACT

The present invention generally relates to compositions, formulations, methods, devices and kits for modulating the production of cerumen, for the treatment and prevention of excessive or impacted cerumen, and for the treatment and prevention of associated diseases, conditions or symptoms resulting from excessive or impacted cerumen.

21 Claims, 4 Drawing Sheets

(56) References Cited

U.S. PATENT DOCUMENTS

| | | |
|---|---|---|
| 7,824,693 B2 | 11/2010 | Sanders |
| 8,034,357 B2 | 10/2011 | Sanders et al. |
| 8,153,139 B1 | 4/2012 | Sanders et al. |
| 8,202,522 B1 | 6/2012 | Sanders et al. |
| 8,779,090 B2 | 7/2014 | Zimmer et al. |
| 8,834,897 B2 | 9/2014 | Sandars |
| 9,128,101 B2 | 9/2015 | Halbert et al. |
| 9,393,187 B2 | 7/2016 | Ferrer Montiel et al. |
| 9,469,876 B2 | 10/2016 | Kuslich et al. |
| 9,683,263 B2 | 6/2017 | Henderson et al. |
| 9,771,392 B2 | 9/2017 | Ferrer Montiel et al. |
| 10,035,820 B2 | 7/2018 | Ferrer Montiel et al. |
| 10,092,580 B2 | 10/2018 | Lichter et al. |
| 10,265,348 B2 | 4/2019 | Soley Astals et al. |
| 2004/0204471 A1* | 10/2004 | Seibert ............... A61K 31/366 514/406 |
| 2006/0079514 A1 | 4/2006 | Preston |
| 2009/0297533 A1 | 12/2009 | Lichter et al. |
| 2014/0163064 A1* | 6/2014 | Melamed ............... A61K 31/46 514/304 |
| 2014/0187635 A1* | 7/2014 | Patel ................... A61K 31/215 514/567 |
| 2018/0000950 A1* | 1/2018 | Savel .................... A61K 47/10 |

OTHER PUBLICATIONS

Sato, Kenzo et al.; "Sweat secretion by human axillary apoeccrine sweat gland in vitro"; American Journal of Physiology—Regulatory, Integrative and Comparative Physiology, vol. 252, No. 1; Jan. 1, 1987; pp. R181-R187.

Stoeckelhuber, Mechthild et al.; "Human ceruminous gland: Ultrastructure and histochemical analysis of antimicrobial and cytoskeletal components"; The Anatomical Record Part A: Discoveries in Molecular, Cellular, and Evolutionary Biology; vol. 288A, No. 8; Aug. 1, 2006; pp. 877-884.

Schiavone, A. et al.; "Muscarinic M receptors mediate secretion from sweat glands in the rat"; Pharmacological Research; vol. 23, No. 3, Apr. 1, 1991; pp. 233-239.

* cited by examiner

COMPOSITIONS AND METHODS FOR CONTROLLING CERUMEN PRODUCTION

FIELD OF THE INVENTION

The present invention generally relates to compositions, formulations, methods, devices and kits for modulating the production of cerumen, for the treatment and prevention of excessive or impacted cerumen, and for the treatment and prevention of associated diseases, conditions or symptoms resulting from excessive or impacted cerumen.

BACKGROUND OF THE INVENTION

Cerumen, commonly known as ear wax, is a hydrophobic protective covering in the ear canal. Cerumen shields the skin of the external ear canal from, for example, water damage, infection, trauma, and foreign bodies.

Under normal conditions, old cerumen is moved out of the ear canal by motions from chewing and other jaw movements. Once the cerumen reaches the outside of the ear canal, it naturally flakes off the skin. Cerumen that does not naturally escape the ear canal may accumulate over time, resulting in partial or full blockage of the ear canal. Cerumen may accumulate in this manner as a result of excess cerumen production by cerumen glands. Cerumen may also build up in the ear as a result of inappropriate ear canal intervention. For example, though light cleaning of the ear canal can be accomplished using a cotton swab, improperly doing so may instead push cerumen farther into the ear canal and lead to canal blockage. Excess cerumen and cerumen impaction, also referred to as ceruminosis, may cause discomfort, symptoms of hearing loss, and local irritation leading to the development of infection.

Excess cerumen and cerumen impaction may also result from hearing aid use, as the hearing aids may impair migration of old cerumen out of the ear. Many hearing aids require placement in the ear canal; however, when inserted, the hearing aid can push cerumen farther into the ear. Moreover, a hearing aid can block the migration of cerumen out of the ear, causing buildup of cerumen between the hearing aid and the eardrum. If built-up cerumen is not properly removed, continued use of a hearing aid may lead to complications including pain and hearing loss.

Cerumen impaction and current treatments of excess cerumen may result in significant complications. For example, otitis externa, pain, dizziness, syncope or fainting, tympanic membrane perforation, ear canal laceration, infection of the ear, and hearing loss are known complications that can occur with ceruminosis treatment regimens routinely used in the current field. As such, there is a need in the art for compositions and methods for treating and/or preventing the formation of excess cerumen in the ear canal.

SUMMARY OF THE INVENTION

In an aspect, the disclosure provides an otic composition for the treatment and prevention of excessive or impacted cerumen comprising as an active ingredient a compound or pharmaceutically acceptable prodrug or salt thereof, wherein the compound is selected from the group consisting of

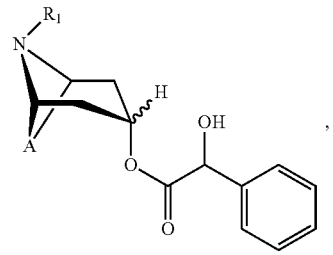

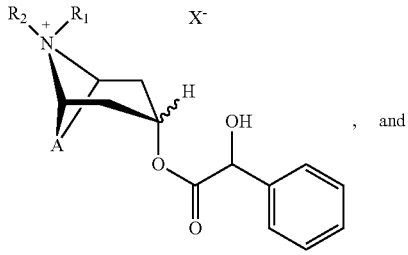

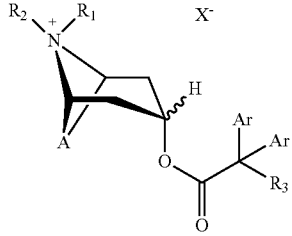

wherein A is a group selected from

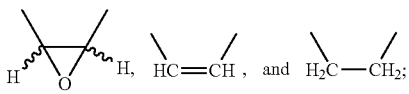

$R^1$ and $R^2$ are each independently hydrogen, $C_1$-$C_4$-alkyl optionally substituted with hydroxy or halogen;

$R^3$ is hydroxy, $C_1$-$C_4$-alkyl, $C_1$-$C_4$-alkoxy, $CF_3$, or fluorine;

$X^-$ denotes an anion selected from among chlorine, bromine, iodine, methanesulphonate or trifluoromethanesulphonate; and Ar is phenyl, naphthyl, thienyl, and furyl, each optionally mono- or disubstituted with one or two groups selected from $C_1$-$C_4$-alkyl, $C_1$-$C_4$-alkoxy, hydroxy, fluorine, chlorine, bromine, or $CF_3$.

The otic composition can further comprise an otologically acceptable carrier. The otologically acceptable carrier of the otic composition can be present in a total amount of not more than about 99.995% by weight of the otic composition. Specifically, the otologically acceptable carrier can be propylene glycol.

The compound of the otic composition having a structure according to formula I, II, or III can be present in the otologically acceptable carrier in dissolved or solubilized form. The compound of the otic composition having a structure according to formula I, II, or III can be present in a total amount of about 0.005% to about 15% by weight of the otic composition.

The otic composition can further comprise or more pharmaceutically active agents selected from anti-bacterial agents, anti-viral agents, anti-fungal agents, disinfectant agents, analgesic agents, immuno-suppressive agents, cerumenolytic agents, vestibular agents, permeability agents, surfactants and premedication agents. The otic composition can be a topical otic solution.

In another aspect, the disclosure provides an otic composition for the treatment and prevention of excessive or impacted cerumen containing a compound of formula IIa

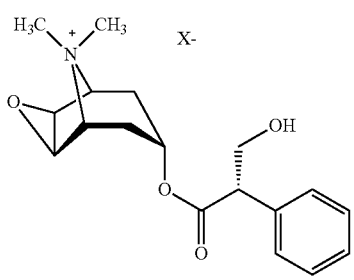

IIa wherein X⁻ denotes an anion selected from among chlorine, bromine, iodine, methanesulphonate or trifluoromethanesulphonate.

In yet another aspect, the disclosure provides an otic composition for the treatment and prevention of excessive or impacted cerumen containing as an active ingredient a compound of formula IIb

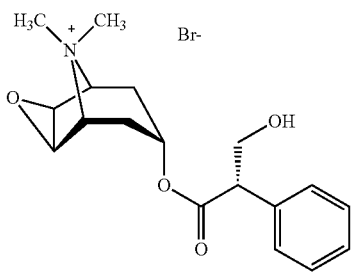

IIb or pharmaceutically acceptable prodrug or salt thereof, comprising otologically acceptable carrier. In another aspect, the disclosure provides an otic composition for the treatment and prevention of excessive or impacted cerumen containing as an active ingredient a compound of formula Ia

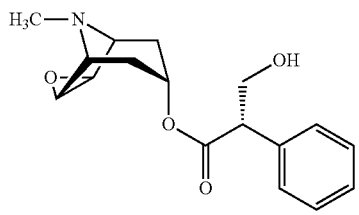

Ia or pharmaceutically acceptable prodrug or salt thereof, comprising otologically acceptable carrier. The compound of the otic composition having a structure according to formula IIb, formula Ia, or a combination thereof, can be present in the ally acceptable carrier in dissolved or solubilized form. The compound of the otic composition having a structure according to formula IIb, formula Ia, or a combination thereof, can be present in a total amount of about 0.005% to about 15% by weight of the otic composition. The ontologically acceptable carrier of the otic composition can be present in a total amount of not more than about 99.995% by weight of the otic composition. Specifically, the otologically acceptable carrier can be propylene glycol.

In still another aspect, the disclosure provides an otic composition for the treatment and prevention of excessive or impacted cerumen comprising a muscarinic antagonist, analog, or derivative thereof, and an otologically acceptable carrier. The muscarinic antagonist, analog, or derivative thereof can be a natural muscarinic antagonist or a synthetic structural analog of atropine selected from the group consisting of atropine, scopolamine, matropine, methscopolamine, ipratropium, and tiotropium. Specifically, the synthetic structural analog of atropine is methscopolamine. Methscopolamine or a pharmaceutically acceptable prodrug or salt thereof can be present in the otic composition in a total amount of about 0.005% to about 15% by weight of the otic composition. The ontologically acceptable carrier of the otic composition can be present in a total amount of not more than about 99.995% by weight of the otic composition. Specifically, the otologically acceptable carrier can be propylene glycol.

In an aspect, the disclosure provides a method of preventing ceruminosis comprising the administration to the external ear canal an otic composition containing a compound or pharmaceutically acceptable prodrug or salt thereof, wherein said compound has a structure according to one of the following formulas;

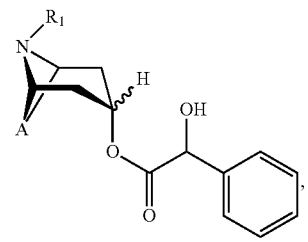

I

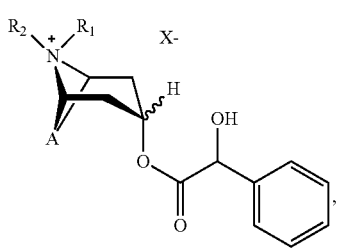

II and

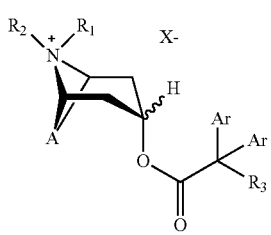

III wherein A is a group selected from

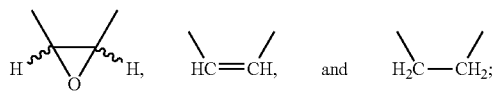

R¹ and R² are each independently hydrogen, $C_1$-$C_4$-alkyl optionally substituted with hydroxy or halogen;

R³ is hydroxy, $C_1$-$C_4$-alkyl, $C_1$-$C_4$-alkoxy, $CF_3$, or fluorine;

$X^-$ denotes an anion selected from among chlorine, bromine, iodine, methanesulphonate or trifluoromethanesulphonate; and Ar is phenyl, naphthyl, thienyl, and furyl, each optionally mono- or disubstituted with one or two groups selected from $C_1$-$C_4$-alkyl, $C_1$-$C_4$-alkoxy, hydroxy, fluorine, chlorine, bromine, or $CF_3$.

The compound of the otic composition having a structure according to formula I, II, or III can be present in a total amount of about 0.005% to about 15% by weight of the otic composition. The otic composition can comprise an ontologically acceptable carrier wherein the ontologically acceptable carrier can be present in a total amount of not more than about 99.995% by weight of the otic composition. Specifically, the otologically acceptable carrier can be propylene glycol.

The otic composition can be topically administered to the external ear and external ear canal. The otic composition can be topically administered by spraying or by instillation, in the form of drops, foam, or gel, into the external ear canal. The otic composition can be administered by a suitable device for irrigation of the external ear canal. Specifically, the otic composition can be topically administered by a suitable device for irrigation of the external ear canal. The otic composition can be administered via medicated ear plugs or sponges by first absorbing the otic composition onto or into the earplug or sponge and then placing the earplug or sponge into the ear for several minutes, several hours or overnight.

The otic composition can be administered to the external ear canal to prevent impacted human cerumen. The otic composition can be administered at least once a day for at least 3 weeks. The otic composition can be administered to the external ear canal at least once a day for at least 3 weeks to treat one or more signs, symptoms or complications of excessive or impacted human cerumen. In other aspects, the otic composition can be administered by a) selecting a subject in need of preventing ceruminosis, wherein the subject in need of preventing ceruminosis is observed to have one or more signs, symptoms or complications of excessive or impacted human cerumen prior to administering the otic composition; b) instructing the selected subject to administer the otic composition at least once a day for 3 weeks; c) observing the selected subject for one or more signs, symptoms or complications of excessive or impacted human cerumen after administering the otic composition for 3 weeks; and d) instructing the selected subject to continue administering the otic composition indefinitely if the one or more signs, symptoms or complications of excessive or impacted human cerumen observed in step a) is attenuated by at least 50% after administering the otic composition for at least 3 weeks. In still other aspects, the otic composition can be administered by a) selecting a subject in need of treating ceruminosis, wherein the subject in need of treating ceruminosis is observed to have one or more signs, symptoms or complications of excessive or impacted human cerumen prior to administering the otic composition; b) instructing the selected subject to administer the otic composition at least once a day for 3 weeks; c) observing the selected subject for one or more signs, symptoms or complications of excessive or impacted human cerumen after administering the otic composition for 3 weeks; and d) instructing the selected subject to continue administering the otic composition for at least an additional 6 months if the one or more signs, symptoms or complications of excessive or impacted human cerumen observed in step a) is attenuated by at least 50% after administering the otic composition for at least 3 weeks;

Administration of otic composition can prevent occlusion of the ear canal, discomfort, decreased hearing, itching, otic fullness, ringing in the ears, hearing aid issues, otitis externa, vertigo, and tinnitus. Specifically, administration of otic composition can prevent at least one hearing aid issue selected from the group of auditory feedback from hearing aid, damage to hearing aid, and pain and/or discomfort with hearing aid use.

In an aspect, the disclosure provides a method of preventing ceruminosis comprising topically administering to the external ear canal an otic composition comprising a methscopolamine or its pharmaceutically acceptable prodrug or salt thereof and an otologically acceptable carrier for at least once a day for at least 3 weeks. Methscopolamine or its pharmaceutically acceptable prodrug or salt thereof, can be present in a total amount of about 0.005% to about 15% by weight of the otic composition. Following administration of the otic composition at least once a day for 3 weeks, cerumen buildup can be reduced by 50%.

In yet another aspect, the disclosure provides a method of preventing excessive cerumen buildup in a subject in need thereof comprising the method comprising; a) removing all cerumen within the external ear canal; b) topically administering to the external ear canal an otic composition comprising a methscopolamine or its pharmaceutically acceptable prodrug or salt thereof and an otologically acceptable carrier after cerumen within the external ear canal is removed; and c) continuing topical administration of the otic composition to the external ear canal at least once a day. Methscopolamine or its pharmaceutically acceptable prodrug or salt thereof, can be present in a total amount of about 0.005% to about 15% by weight of the otic composition.

DETAILED DESCRIPTION OF THE INVENTION

Figure 1A:
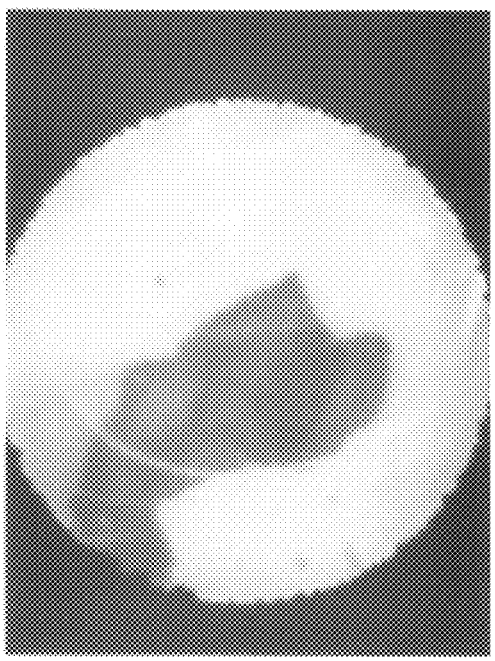
FIG. 1A depicts an image of a subject's left ear that was not cleaned for 6 months resulting in excessive wax accumulation which blocked complete visualization of tympanic membrane.

Compositions comprised of a combination of ingredients directed toward treating and/or preventing excessive or impacted cerumen are detailed below. In general, the compositions disclosed herein comprise one or more muscarinic antagonists. In various embodiments, compositions of the present disclosure comprise one or more muscarinic antagonists in an otologically acceptable carrier. In various embodiments, compositions of the present disclosure may treat or prevent one or more symptoms associated with excessive or impacted cerumen.

(I) Compositions

One aspect of the present disclosure encompasses a composition containing as an active ingredient one or more muscarinic antagonists. As used herein, the term "active ingredient" can include one or more compounds intended to furnish pharmacological activity or other direct and/or indirect effect in the treatment and/or prevention of excessive or impacted cerumen. A composition disclosed herein may further comprise an otologically acceptable carrier. A composition disclosed herein may further comprise one or more excipients.

(a) Muscarinic Antagonist Compounds

In various embodiments, compositions disclosed herein comprise at least one or more muscarinic antagonist compounds. As used herein, a "muscarinic antagonist compound" is a type of anticholinergic compound that blocks the activity of the muscarinic acetylcholine receptor. In various embodiments, compositions disclosed herein comprise at least one or more muscarinic antagonist compounds of the general formulas;

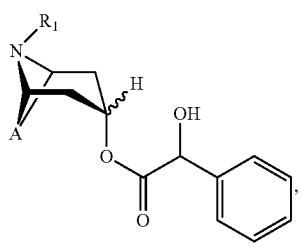

I

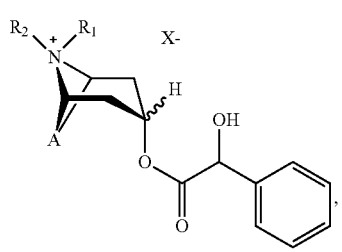

II and

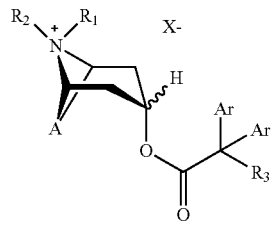

III wherein A is a group selected from

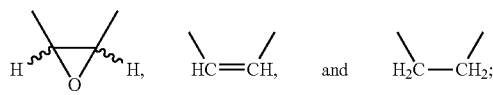

$R^1$ and $R^2$ are each independently hydrogen, $C_1$-$C_4$-alkyl optionally substituted with hydroxy or halogen;

$R^3$ is hydroxy, $C_1$-$C_4$-alkyl, $C_1$-$C_4$-alkoxy, $CF_3$, or fluorine;

$X^-$ denotes an anion selected from among chlorine, bromine, iodine, methanesulphonate or trifluoromethanesulphonate; and Ar is phenyl, naphthyl, thienyl, and furyl, each optionally mono- or disubstituted with one or two groups selected from $C_1$-$C_4$-alkyl, $C_1$-$C_4$-alkoxy, hydroxy, fluorine, chlorine, bromine, or $CF_3$.

In additional embodiments, the dichromic compound comprises Formula (IIa);

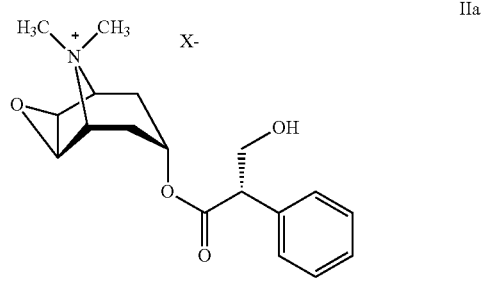

IIa wherein $X^-$ denotes an anion selected from among chlorine, bromine, iodine, methanesulphonate or trifluoromethanesulphonate.

In preferred embodiments, the dichromic compound comprises Formula (IIb);

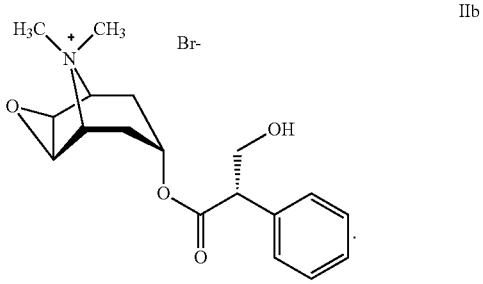

IIb

In preferred embodiments, the dichromic compound comprises Formula (Ia)

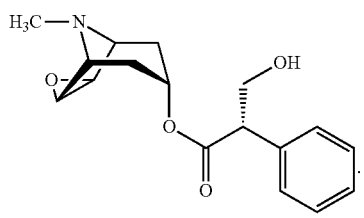

Ia

Unless otherwise stated, the alkyl groups are straight-chained or branched alkyl groups having 1 to 4 carbon atoms. The following are mentioned by way of example; methyl, ethyl, propyl, or butyl. In some cases the abbreviations Me, Et, Prop, or Bu are used to denote the groups methyl, ethyl, propyl, or butyl. Unless otherwise stated, the definitions propyl and butyl include all the possible isomeric forms of the groups in question. Thus, for example, propyl includes n-propyl and isopropyl, butyl includes isobutyl, sec-butyl, and tert-butyl, etc.

Unless otherwise stated, the term alkyloxy groups denotes branched and unbranched alkyl groups having 1 to 4 carbon atoms which are linked via an oxygen atom. Examples of these include; methyloxy, ethyloxy, propyloxy, or butyloxy. The abbreviations MeO-, EtO-, PropO-, or BuO- are used in some cases to denote the groups methyloxy, ethyloxy, propyloxy, or butyloxy. Unless otherwise stated, the definitions propyloxy and butyloxy include all possible isomeric forms of the groups in question. Thus, for example, propyloxy includes n-propyloxy and isopropyloxy, butyloxy includes isobutyloxy, sec-butyloxy, and tert-butyloxy, etc. In some cases, within the scope of the present invention, the term alkoxy is used instead of the term alkyloxy. Accordingly, the terms methoxy, ethoxy, propoxy, or butoxy may also be used to denote the groups methyloxy, ethyloxy, propyloxy, or butyloxy.

Halogen within the scope of the present invention denotes fluorine, chlorine, bromine, or iodine. Unless stated otherwise, bromine is the preferred halogen.

Muscarinic antagonist compounds suitable for compositions disclosed herein may comprise one or more muscarinic antagonist compound derivative, variant, free acid, free base, pharmaceutically acceptable prodrug, or salt thereof. As used herein, "pharmaceutically acceptable salts" refer to derivatives of the muscarinic antagonist compounds wherein the therapeutic muscarinic antagonist compound is modified by making acid or base salts thereof. Examples of pharmaceutically acceptable salts include, but are not limited to, mineral or organic acid salts of the muscarinic antagonist compound. Pharmaceutically acceptable salts may include, but are not limited to, conventional non-toxic salts, for example, from non-toxic inorganic or organic acids. For example, such conventional non-toxic salts may include, but are not limited to, those derived from inorganic acids such as hydrochloric, hydrobromic, sulfuric, sulfonic, sulfamic, phosphoric, nitric and others known to those of ordinary skill in the art; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy benzoic, fumaric, toluenesulfonic, methanesulfonic, ethane disulfonic, oxalic, isethionic, and other known to those of ordinary skill in the pharmaceutical sciences. For acidic compounds, a salt may include, but is not limited to, an amine-based (primary, secondary, tertiary or quaternary amine) counter ion, an alkali metal cation, or a metal cation. Lists of suitable salts may be found in texts such as *Remington's Pharmaceutical Sciences,* 18th Ed. (Alfonso R. Gennaro, ed.; Mack Publishing Company, Easton, PA, 1990); *Remington; the Science and Practice of Pharmacy.* 19th Ed. (Lippincott, Williams & Wilkins, 1995); *Handbook of Pharmaceutical Excipients,* 3rd Ed. (Arthur H. Kibbe, ed.; Amer. Pharmaceutical Assoc., 1999); the *Pharmaceutical Codex; Principles and Practice of Pharmaceutics.* 12th Ed. (Walter Lund ed.; Pharmaceutical Press, London, 1994); *The United States Pharmacopeia; The National Formulary* (United States Pharmacopeial Convention); and *Goodman and Gilman's; the Pharmacological Basis of Therapeutics* (Louis S. Goodman and Lee E. Limbird, eds.; McGraw Hill, 1992), the disclosures of which are hereby incorporated by reference.

In another aspect, compositions disclosed herein may comprise naturally-occurring muscarinic antagonist compounds. In preferred aspects, natural muscarinic antagonist compounds may be atropine or scopolamine. In another aspect, compositions disclosed herein may comprise synthetic muscarinic antagonist compounds. As used herein the term "synthetic muscarinic antagonist compounds" encompasses all non-naturally derived or formulated muscarinic antagonist compounds, including but not limited to pharmaceutical grade muscarinic antagonist compounds. In some aspects, synthetic muscarinic antagonist compounds may be a synthetic structural analog of atropine. In preferred aspects the synthetic structural analog of atropine may be homatropine, methscopolamine, ipratropium, or tiotropium.

In various embodiments, a composition disclosed herein may comprise about 0.005% to about 15%, about 0.01% to about 14%, or about 0.02% to about 10% total muscarinic antagonist compound by total weight of the composition. In other embodiments, a composition disclosed herein may comprise about 0.005%, about 0.01%, about 0.02% about 0.05%, about 0).1%, about 0.5%, about 1%, about 5%, about 10%, or about 15% total muscarinic antagonist compound by total weight of the composition.

In embodiments in which a composition of the present disclosure comprises one or more muscarinic antagonist compounds, examples of suitable muscarinic antagonist compounds include, but are not limited to, methscopolamine, scopolamine, atropine, hyoscyamine, hyoscine, hydrobromide, hyoscine butylbromide, ipratropium., tropicamide, cyclopentolate, pirenzepine, diphenhydramine, doxylamine, dimenhydrine, dicyclomine, flavoxate, oxybutynin, tiotropium, cyclopentolate, atropine methonitrate, trihyxyphenidyl, tolterodine, solifenacin, darifenacin, benzatropine, mebeverine, procyclidine, aclidinium bromide, and the like. In various embodiments, muscarinic antagonist compounds used in compositions disclosed herein may comprise one or more of methscopolamine, scopolamine, atropine, glycopyrronium, hyoscyamine, hyoscine, hydrobromide, hyoscine butylbromide, ipratropium, tropicamide, cyclopentolate, pirenzepine, diphenhydramine, doxylamine, dimenhydrine, dicyclomine, flavoxate, oxybutynin, tiotropium, cyclopentolate, atropine methonitrate, trihyxyphenidyl, tolterodine, solifenacin, darifenacin, benzatropine, mebeverine, procyclidine, and aclidinium bromide. In other embodiments, muscarinic antagonist compounds used in compositions disclosed herein may comprise one or more of methscopolamine, scopolamine, glycopyrronium, and atropine. In a preferred embodiment, the muscarinic antagonist compound used in compositions disclosed herein may be methscopolamine.

(b) Pharmaceutically Acceptable Carriers and Excipients

In various embodiments, compositions disclosed herein may further compromise one or more pharmaceutically acceptable diluent(s), excipient(s), or carrier(s). As used herein, a pharmaceutically acceptable diluent, excipient, or carrier, refers to a material suitable for administration to a subject without causing undesirable biological effects or interacting in a deleterious manner with any of the components of the composition in which it is contained. Pharmaceutically acceptable diluents, carriers, and excipients include, but are not limited to, water, physiological saline, Ringer's solution, phosphate solution or buffer, buffered saline, and other carriers known in the art. Pharmaceutical compositions may also include stabilizers, anti-oxidants, colorants, other medicinal or pharmaceutical agents, carriers, adjuvants, preserving agents, stabilizing agents, wetting agents, emulsifying agents, solution promoters, salts, solubilizers, antifoaming agents, antioxidants, dispersing agents, surfactants, and combinations thereof.

In various embodiments, compositions disclosed herein may comprise solids, liquids, suspensions, dispersions, gels, syrups, pastes, ointments, creams, powders, jellies, hydrogels, nano- or micro-particles, drops or other carriers or formulations suitable for otic administration. In other embodiments, compositions disclosed herein may comprise an otologically acceptable carrier. As used herein, the term "otologically acceptable carrier" refers to any substance or combination of substances that act as a carrier for an active agent or agents and that are suitable for administration to the external ear canal. In various embodiments, a composition disclosed herein may comprise about 0.005% to about 99.995% otologically acceptable carrier agent(s) by total weight of the composition. In other embodiments, a composition disclosed herein may comprise about 50%, about 75%, about 80%, about 85%, about 90%, or about 95% otologically acceptable carrier agent(s) by total weight of the composition. In other embodiments, a composition disclosed herein may comprise about 99%, about 99.1%, about 99.2%, about 99.3%, about 99.4%, about 99.5%, about 99.5%, about 99.7%, about 99.8%, or about 99.9% otologically acceptable carrier agent(s) by total weight of the composition.

In an aspect, an otologically acceptable carrier may be aqueous or nonaqueous or a mixture of nonaqueous substances and aqueous substances. Suitable otologically acceptable carriers include, but are not limited to, water, hydrophilic solvents, hydrophobic solvents, monomeric polyols, polymeric polyols, and a mixture thereof. As used herein, the term "monomeric polyol" refers to a compound with 2 to 6 carbon atoms and at least two hydroxy groups. Non-limiting examples of monomeric polyols are glycerin, propylene glycol, ethylene glycol, sorbitol and mannitol. In an aspect, the monomeric polyols are selected from polyols having 2-3 carbons and at least two hydroxy groups ("2-3 carbon polyol"). Non-limiting examples of 2-3 carbon polyols are glycerin, 1,2-propane diol ("propylene glycol"), and 1,3-propane diol. In a preferred embodiment, the 2-3 carbon polyol is propylene glycol. As used herein, the term "polymeric polyol" refers to a polyalkoxylated glycol with a molecular weight ranging from about 200-600 Daltons. Non-limiting examples of polymeric polyols are polyethylene glycol 200 (denoting a molecular weight of 200 Daltons, "PEG 200") and PEG 400. In an aspect, the PEGs used herein may optionally be monoalkoxylated. Non-limiting examples of monoalkoxylated PEGs are monomethoxy PEG 200 and ethoxy PEG 400. In some embodiments, a suitable otologically acceptable carrier may comprise a combination of monomeric and polymeric polyols. In an aspect, the ratio of monomeric polyols to polymeric polyols may be from 1:5 to 5:1. In a preferred embodiment, compositions disclosed herein comprise propylene glycol as the otologically acceptable carrier.

In other aspects, an otologically acceptable carrier may be oil comprising at least one cannabinoid. Cannabinoids may be extracted from the *cannabis* plant using methods well-established in the art. Many of the cannibinoids may also be prepared using standard chemical synthetic methods. Some of these compounds are also commercially available. Examples of cannibinoids include, but are not limited to, cannabidiol (CBD), cannabidiol acid (CBDA), cannabinol (CBN), cannabigerol (CBG), cannabigerol acid (CBGA), cannabidivarin (CBDV), cannabidivarin acid (CBDVA), cannabinovarin (CBNV), cannabigerovarin (CBGV), cannabichromene (CBC), naphthoylindoles such as JWH-018, JWH-073, JWH-398, JWH-200, JWH-081, 4-methyl-JWH-073, JWH-015, JWH-122, JWH-220. JWH-019, JWH-007; phenylacetylindoles such as JWH-250) and JWH-203; benzoylindoles such as RCS-4, AM-694 and WIN 48,098; cyclohexylphenoles such as CP 47,497-$C_8$ and CP 47,497; and HU-210.

"Carrier materials" are excipients that are compatible with active agents described herein, the targeted auris structure(s) and the release profile properties of the compositions and formulations disclosed herein. As used herein, the term "auris structure" refers to portion of the ear. In some aspects, an auris structure may be auris interna (inner ear), auris externa (outer ear), middle ear (auris media), or any structure encompassed in at one of these portions of the ear. In other aspects, an auris structure may be an ear canal, an ear drum, an ossicular chain, a vestibule, a cochlea, or an eustachian tube. In some aspects, carrier materials may include, e.g., binders, suspending agents, disintegration agents, filling agents, surfactants, solubilizers, stabilizers, lubricants, wetting agents, diluents, and the like. Carrier materials compatible with compositions and formulations disclosed herein can include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

In various embodiments, compositions disclosed herein may comprise a viscous formulation. In an aspect, viscosity of the composition may be increased by the addition of one or more gelling or thickening agents. In an aspect, compositions disclosed herein may comprise one or more gelling or thickening agents in an amount to provide a sufficiently viscous formulation to remain on treated tissue. In another aspect, compositions disclosed herein may comprise at most 5%, at most 10%, at most 20%, at most 25%, at most 30%, at most 35%, at most 40%, at most 45%, at most 50% total amount of gelling or thickening agent(s) by total weight of the composition. In still another aspect, suitable thickening agents include hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted auris structure include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), *ceratonia*, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP; povidone), SplendaR; (dextrose, maltodextrin and sucralose) or combinations thereof. In specific embodiments, suitable thickening agent may be carboxymethyl-cellulose.

In another aspect, compositions disclosed herein may comprise one or more gelling or thickening agents wherein the total concentration of gelling or thickening agents is sufficient increase viscosity of the composition. Viscosity in a composition may be expressed in units of centipoise (cP). Viscosity may be measured using methods commonly known in the art. In preferred embodiments, a LVDV-II+CP Cone Plate Viscometer and a Cone Spindle CPE-40 are used to calculate the viscosity of the compositions disclosed herein.

In another aspect, compositions disclosed herein may comprise one or more gelling or thickening agents wherein the total concentration of gelling or thickening agents is sufficient to provide an apparent viscosity from about 100 to about 100,000 cP. In some embodiments, an apparent viscosity of a composition disclosed herein may range from about 100 cP to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, or about 15,000 cP to about 1,000,000 cP. In some embodiments, the viscosity ranges referred to herein are measured at room temperature. In other embodiments, the viscosity ranges referred to herein are measured at body temperature (e.g., at the average body temperature of a healthy human).

In various embodiments, compositions disclosed herein may comprise additional agents or additives selected from a group including surface-active agents, detergents, solvents, acidifying agents, alkalizing agents, buffering agents, tonicity modifying agents, ionic additives effective to increase the ionic strength of the solution, antimicrobial agents, antibiotic agents, antifungal agents, antioxidants, preservatives, electrolytes, antifoaming agents, oils, stabilizers, enhancing agents, and the like. In an aspect, compositions disclosed herein may comprise at most 5%, at most 10%, at most 20%, at most 25%, at most 30%, at most 35%, at most 40%, at most 45%, at most 50% total amount of one or more agents by total weight of the composition. In another aspect, one or more of these agents may be added to improve the performance, efficacy, safety, shelf-life and/or other property of the muscarinic antagonist composition of the invention. In a preferred aspect, additives will be biocompatible, and will not be harsh, abrasive, or allergenic.

In various embodiments, compositions disclosed herein may comprise one or more acidifying agents. As used herein, "acidifying agents" refers to compounds used to provide an acidic medium. Such compounds include, by way of example and without limitation, acetic acid, amino acid, citric acid, fumaric acid and other alpha hydroxy acids, such as hydrochloric acid, ascorbic acid, and nitric acid and others known to those of ordinary skill in the art. In an aspect, any pharmaceutically acceptable organic or inorganic acid may be used. In another aspect, compositions disclosed herein may comprise at most 5%, at most 10%, at most 20%, at most 25%, at most 30%, at most 35%, at most 40%, at most 45%, at most 50% total amount of one or more acidifying agents by total weight of the composition.

In various embodiments, compositions disclosed herein may comprise one or more alkalizing agents. As used herein, "alkalizing agents" are compounds used to provide alkaline medium. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art. In an aspect, any pharmaceutically acceptable organic or inorganic base can be used. In another aspect, compositions disclosed herein may comprise at most 5%, at most 10%, at most 20%, at most 25%, at most 30%, at most 35%, at most 40%, at most 45%, at most 50% total amount of one or more alkalizing agents by total weight of the composition.

In various embodiments, compositions disclosed herein may comprise one or more antioxidants. As used herein, "antioxidants" are agents that inhibit oxidation and thus can be used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and other materials known to one of ordinary skill in the art. In another aspect, compositions disclosed herein may comprise at most 5%, at most 10%, at most 20%, at most 25%, at most 30%, at most 35%, at most 40%, at most 45%, at most 50% total amount of one or more antioxidants by total weight of the composition.

In other embodiments, compositions disclosed herein may comprise a buffer system. As used herein, a "buffer system" is a composition comprised of one or more buffering agents wherein "buffering agents" are compounds used to resist change in pH upon dilution or addition of acid or alkali. Buffering agents include, by way of example and without limitation, potassium metaphosphate, potassium phosphate, monobasic sodium acetate and sodium citrate anhydrous and dihydrate and other materials known to one of ordinary skill in the art. In an aspect, any pharmaceutically acceptable organic or inorganic buffer can be used. In another aspect, compositions disclosed herein may comprise at most 5%, at most 10%, at most 20%, at most 25%, at most 30%, at most 35%, at most 40%, at most 45%, at most 50% total amount of one or more buffering agents by total weight of the composition. In still another aspect, the amount of one or more buffering agents may depend on the desired pH level of a composition. In an aspect, compositions disclosed herein further comprising one or more buffering agents may maintain a pH of the cleansing composition at the desired level during storage of the composition. In an aspect, compositions disclosed herein further comprising one or more buffering agents may maintain the pH of the composition after it is topically applied and exposed to the environment. In some embodiments, compositions disclosed herein may have a pH of about 1 to about 10, about 2 to about 9, about 3 to about 8, or about 4 to about 6. In some embodiments, compositions disclosed herein may have a pH greater than about 9, greater than about 8, greater than about 8.5, greater than about 8, greater than about 7.5, greater than about 7, greater than about 6.5, greater than about 6, greater than about 5.5, greater than about 5, greater than about 4.5, greater than about 4, greater than about 3.5, greater than about 3, greater than about 2.5, greater than about 2, or greater than about 1.5. In a preferred embodiment, compositions disclosed herein may have a pH greater than about 1.9.

In some embodiments, compositions described herein can be stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations described herein are stable with respect to pH over a period of at least about 1 week. Also described herein are compositions that can be stable with respect to pH over a period of at least about 1 month.

In various embodiments, compositions disclosed herein may comprise one or more preservatives. As used herein, "preservatives" refers to agents or combination of agents that inhibits, reduces or eliminates bacterial growth in a pharmaceutical dosage form. In some embodiments, compositions disclosed herein may alternatively or additionally contain at least one preservative to prevent microbial growth. Suitable preservatives for use in the compositions and formulations disclosed herein include, but are not limited to benzoic acid, boric acid, p-hydroxy benzoates, alcohols, quarternary compounds, stabilized chlorine dioxide, mercurials, such as merfen and thiomersal, mixtures of the foregoing and the like.

In further embodiments, the preservative is, by way of example only, an antimicrobial agent, within the compositions and formulations presented herein. In other embodiments, the formulation can include a preservative such as by way of example only, methyl paraben, sodium bisulfite, sodium thiosulfate, ascorbate, chorobutanol, thimerosal, parabens, benzyl alcohol, phenylethanol and others. In other embodiments, the methyl paraben can be at a concentration of about 0.05% to about 1.0% or about 0.1% to about 0.2%. In further embodiments, the formulation may be prepared by mixing water, methylparaben, hydroxyethylcellulose and sodium citrate. In further embodiments, the formulation may be prepared by mixing water, methylparaben, hydroxyethylcellulose and sodium acetate. In further embodiments, the mixture can be sterilized by autoclaving at about 120° C. for about 20 minutes, and tested for pH, methylparaben concentration and viscosity before mixing with the appropriate amount of the active ingredient disclosed herein.

In some embodiments, compositions disclosed herein can include at least one auris-acceptable water soluble preservative in a drug delivery vehicle disclosed herein. In some aspects, an auris-acceptable water soluble preservative in the drug delivery vehicle may be in amounts of about 0.001% to about 5% by weight and, preferably, in the amount of about 0.01 to about 2% by weight. In some embodiments, compostions and formulations disclosed herein are free of preservatives. Non-limiting examples of preservatives suited for use herein include benzalkonium chloride, benzalkonium bromide, sodium bisulfite, sodium thiosulfate, ascorbate, chorobutanol, thimerosal, parabens, benzyl alcohol, butylated hydroxytoluene (BHT), Nipagin, Nipasol, isopropyl alcohol, or a combination thereof. In an aspect, any pharmaceutically acceptable preservative can be used. In another aspect, compositions disclosed herein may comprise at most 5%, at most 10%, at most 20%, at most 25%, at most 30%, at most 35%, at most 40%, at most 45%, at most 50% total amount of one or more preservatives by total weight of the composition.

In other embodiments, compositions disclosed herein may comprise one or more surface-acting reagents, surfactants, or detergents. In an aspect, surface-acting reagents. Surface-acting reagents, surfactants, or detergents may be synthetic, natural, or semi-synthetic. In an aspect, compositions disclosed herein may comprise anionic detergents, cationic detergents, zwitterionic detergents, ampholytic detergents, amphoteric detergents, nonionic detergents having a steroid skeleton, or a combination thereof. In other aspects, compositions disclosed herein may comprise at least one otically acceptable surface-acting reagent, surfactant, or detergent selected from the group comprising; sodium lauryl sulfate; sodium decussate; Tween 60 or 80; triacetin; vitamin E TPGS; phospholipids; lecithins; phosphatidyl cholines (c8-c18); phosphatidylethanolamines (c8-c18); phosphatidylglycerols (c8-c18); sorbitan monooleate; polyoxyethylene sorbitan monooleate; polysorbates; polaxomers; bile salts; glyceryl monostearate; copolymers of ethylene oxide and propylene oxide, e.g., Pluronic® (BASF); polyoxyethylene fatty acid glycerides and vegetable oils, e.g., polyoxyethylene (60) hydrogenated castor oil; and, polyoxyethylene alkylethers and alkylphenyl ethers, e.g., octoxynol 10, octoxynol 40. In some aspects, surface-acting reagents, surfactants, or detergents can be included to enhance physical stability or for other purposes. In other aspects, compositions disclosed herein may comprise at most 5%, at most 10%, at most 20%, at most 25%, at most 30%, at most 35%, at most 40%, at most 45%, at most 50% total amount of one or more surface-acting reagents or detergents by total weight of the composition. In a preferred aspect, compositions disclosed herein may comprise polysorbate 20.

In various embodiments, compositions disclosed herein may comprise one or more stabilizers. As used herein, a "stabilizer" refers to a compound used to stabilize an active agent against physical, chemical, or biochemical process that would otherwise reduce the therapeutic activity of the agent. In some aspects, stabilizers can be any antioxidation agents, buffers, acids, preservatives and the like that are compatible with the environment of the targeted auris structure. Stabilizers include but are not limited to agents that may (1) improve the compatibility of excipients with a container, or a delivery system, including a Syringe or a glass bottle, (2) improve the stability of a component of the composition, (3) improve formulation stability, or a combination thereof. Suitable stabilizers include, by way of example and without limitation, succinic anhydride, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art. In an aspect, compositions disclosed herein may comprise at most 5%, at most 10%, at most 20%, at most 25%, at most 30%, at most 35%, at most 40%, at most 45%, at most 50% total amount of one or more stabilizers by total weight of the composition.

In other embodiments, compositions disclosed herein may comprise one or more tonicity agents. As used herein, a "tonicity agents" refers to a compound that can be used to adjust the tonicity of the liquid formulation. Suitable tonicity agents include, but are not limited to, glycerin, lactose, mannitol, dextrose, sodium chloride, sodium sulfate, sorbitol, trehalose and others known to those or ordinary skill in the art. Osmolarity in a composition may be expressed in milliosmoles per liter (mOsm/L). Osmolarity may be measured using methods commonly known in the art. In preferred embodiments, a vapor pressure depression method is used to calculate the osmolarity of the compositions disclosed herein.

In an aspect, the amount of one or more tonicity agents comprising a composition disclosed herein may result in a composition osmolarity of about 150 mOsm/L to about 500 mOsm/L, about 250) mOsm/L to about 500 mOsm/L, about 250 mOsm/L to about 350 mOsm/L, about 280) mOsm/L to about 370) mOsm/L or about 250) mOsm/L to about 320) mOsm/L. In another aspect, a composition herein may have an osmolality ranging from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320) mOsm/kg, or from about 250) mOsm/kg to about 350 mOsm/kg or from about 280 mOsm/kg to about 320 mOsm/kg. In some embodiments, a composition described herein has an osmolarity of about 100 mOsm/L to about 1000 mOsm/L, about 200 mOsm/L to about 800 mOsm/L, about 250 mOsm/L to about 500 mOsm/L, about 250) mOsm/L to about 350 mOsm/L, about 250) mOsm/L to about 320 mOsm/L, or about 280) mOsm/L to about 320 mOsm/L. In an aspect, compositions disclosed herein may comprise at most 5%, at most 10%, at most 20%, at most 25%, at most 30%, at most 35%, at most 40%, at most 45%, at most 50% total amount of one or more toxicity modifiers by total weight of the composition.

In other embodiments, compositions disclosed herein may comprise one or more antifoaming agents. As used herein, an "antifoaming agent" refers to a compound that prevents or reduces the amount of foaming that might form on the surface of a composition. Suitable antifoaming agents include by way of example and without limitation, dimethicone, simethicone, octoxynol and others known to those of ordinary skill in the art. In an aspect, compositions disclosed herein may comprise at most 5%, at most 10%, at most 20%, at most 25%, at most 30%, at most 35%, at most 40%, at most 45%, at most 50% total amount of one or more antifoaming agents by total weight of the composition.

In various embodiments, compositions disclosed herein may comprise one or more enhancing agents. As used herein, an "enhancing agent" refers to a compound that aids in an increase or prolongation of either the potency or duration of a desired effect of a muscarinic antagonist, or a diminution of any adverse symptomatology that is consequent upon the administration of the therapeutic agent. In an aspect, compositions disclosed herein may comprise at most 5%, at most 10%, at most 20%, at most 25%, at most 30%, at most 35%, at most 40%, at most 45%, at most 50% total amount of one or more enhancing agents by total weight of the composition. In other aspects, an enhancing agent can include dimethylsulfoxide (DMSO) or a combination of pluronic lecithin organizer (PLO) and DMSO. Further, an enhancing agent may include, but is not limited to, alcohols, such as short chain alcohols, long chain alcohols, or polyalcohols; amines and amides, such as urea, amino acids or their esters, amides, AZONER; (n-dodecyl-caprolactam), derivatives of AZONER, pyrrolidones, or derivatives of pyrrolidones; terpenes and derivatives of terpenes; fatty acids and their esters; macrocyclic compounds; tensides; or sulfoxides other than dimethylsulfoxide, such as, decylmethylsulfoxide; liposomes; transfersomes; lecithin vesicles; ethosomes; water; surfactants, such as anionic, cationic, and nonionic surfactants; polyols; and essential oils.

(c) Dosage Formulations

In various embodiments, compositions disclosed herein may be formulated for local administration. As used herein, "local administration" refers to administration of one or more compositions disclosed herein directly to, in, or to the vicinity of, the ear or ear region to be treated. In some aspects, local administration of compositions disclosed herein may include topical administration, otic intramuscular administration, or a combination thereof. In various embodiments, compositions disclosed herein may be topical formulations. Topical formulations suitable for use herein may be prepared as disclosed in *Electrically Assisted Transdermal and Topical Drug Delivery* (ed. A. K. Banga; 1998); *Topical Drug Bioavailability. Bioequivalence and Penetration* (ed. V. P. Shah; 1993); *Topical Drug Delivery Formulations* (ed. D. W. Osborne); *Transdermal and Topical Drug Delivery Systems* (ed. T. K. Ghosh; 1997); and other publications known to those of ordinary skill in the art, the entire disclosures of which are hereby incorporated by reference, and modified as described herein to include one or more muscarinic antagonists. The muscarinic antagonists described herein can be incorporated into any topical formulation known in the art. In preferred embodiments, the compositions disclosed herein are topical otic formulations.

In various embodiments, otic formulations disclosed herein may comprise any otologically acceptable materials. In an aspect, otic formulations disclosed herein may be a spray, drops solution, suspension, dispersion, a gel, syrup, a paste, an ointment, a cream, a hydrogel, a fluid, foam, powders or any other otologically acceptable form. In another aspect, otic formulations described herein may provide a controlled, constant, sustained, instant, extended, or delayed rate of release of an active agent into the external ear canal environment. Suitable prior art formulations that may be modified according to the disclosure herein include all formulations suitable for otic administration. Specific embodiments of such formulations are disclosed in U.S. Pat. Nos. 6,417,179, 4,895,875, 4,769,171, 5,296,472, 5,380, 711, and 4,169,065, the entire disclosures of which are hereby incorporated by reference. In some aspects, suitable formulations that can be modified according to the invention may be disclosed in the scientific literature. In other aspects, commercially available compositions used to cleanse cerumen from the ear canal can be modified to include one or more muscarinic antagonists to prepare a composition according to the invention. Non-limiting examples of suitable commercial formulations include those sold under the trademarks DEBROX™ (carbamide peroxide otic solution; SmithKline Beecham), AURO™ (carbamide peroxide otic solution; Del Pharmaceuticals, Inc.), BAUSCH & LOMB Earwax Removal System (Bausch & Lomb Incorporated), E-R-O™ Earwax Removal Drops (carbamide peroxide otic solution; Scherer Labs), MURINE Earwax Removal System (carbamide peroxide otic solution), and EAR-CLEAR™ (carbamide peroxide otic solution).

(d) Combination Therapy

In various embodiments, compositions disclosed herein may further comprise one or more active pharmaceutical ingredients in combination with one or more muscarinic antagonists. In an aspect, compositions disclosed herein may comprise at most 5%, at most 10%, at most 20%, at most 25%, at most 30%, at most 35%, at most 40%, at most 45%, at most 50% total amount of one or more active pharmaceutical ingredients by total weight of a composition comprising muscarinic antagonists. In some embodiments, compositions disclosed herein may further comprise antibiotics, anti-fungal, cortical steroids, non-steroidal anti-inflammatoires, anti-parasites, or combinations thereof, among others.

In some embodiments, antibiotics for use within the compositions disclosed herein include aminoglycosides, amikacin, gentamicin, kanamycin, neomycin, netilmicin, tobramycin, paromomycin, spectinomycin, ansamycins, geldanamycin, herbimycin, rifaximin, carbacephem, loracarbef, carbapenems, ertapenem, doripenem, meropenem, cephalosporins, cefadroxil, cefazolin, cefalotin, cefalexin, cephalosporins, cefaclor, cefamandole, cefoxitin, cefprozil, cefuroxime, cephalosporins, cefixime, cefdinir, cefditoren, cefoperazone, cefotaxime, cefpodoxime, ceftazidime, ceftibuten, ceftizoxime, ceftriaxone, cephalosporins, cefepime, cephalosporins, ceftaroline fosamil, ceftobiprole, glycopeptides, teicoplanin, vancomycin, telavancin, lincosamides, clindamycin, lincomycin, lipopeptide, daptomycin, macrolides, azithromycin, clarithromycin, dirithromycin, erythromycin, roxithromycin, troleandomycin, telithromycin, spiramycin, monobactams, aztreonam, nitrofurans, furazolidone, nitrofurantoin, oxazolidonones, linezolid, posizolid, radezolid, torezolid, penicillins, amoxicillin, ampicillin, azlocillin, carbenicillin, cloxacillin, dicloxacillin, flucloxacillin, mezlocillin, methicillin, nafcillin, oxacillin, penicillin, piperacillin, temocillin, ticarcillin, polypeptides, bacitracin, colistin, polymyxin b, quinolones, ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin, sulfonamides, mafenide, sulfadiazine, sulfamethizole, sulfamethoxazole, sulfanilimide (archaic), sulfasalazine, sulfisoxazole, tetracyclines, demeclocycline, doxycycline, minocycline, oxytetracycline, tetracycline, clofazimine, dapsone, capreomycin, cycloserine, ethambutol, ethionamide, isoniazid, pyrazinamide, rifabutin, rifapentine, streptomycin, arsphenamine, chloramphenicol, fosfomycin, metronidazole, mupirocin, quinupristin/dalfopristin, thiamphenicol, tigecycline, trimethoprim, and combinations thereof, among others.

In other embodiments, antifungals for use within the compositions disclosed herein include amrolfine, utenafine, naftifine, terbinafine, flucytosine, fluconazole, itraconazole, ketoconazole, posaconazole, ravuconazole, voriconazole, clotrimazole, econazole, miconazole, oxiconazole, sulconazole, terconazole, tioconazole, nikkomycin Z, caspofungin, micafungin, anidulafungin, amphotericin B, liposomal nystastin, pimaricin, griseofulvin, ciclopirox olamine, haloprogin, tolnaftate, undecylenate, clioquinol, and combinations thereof, among others.

In still other embodiments, antivirals for use within the compositions disclosed herein include acyclovir, famciclovir, valacyclovir, abacavir, aciclovir, adefovir, amantadine, amprenavir, arbidol., atazanavir, artipla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, immunovir, idoxuridine, imiquimod, indinavir, inosine, integrase inhibitors, interferons, including interferon type III, interferon type II, interferon type I, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof, among others.

In other embodiments, cortical steroids for use within the compositions disclosed herein include hydrocortisone, prednisone, fluprednisolone, triamcinolone, dexamethasone, betamethasone, cortisone, prednilosone, methylprednisolone, fluocinolone acetonide, flurandrenolone acetonide, and fluorometholone, among others.

In some other embodiments, anti-parasites for use within the compositions disclosed herein include amitraz, amoscanate, avermectin, carbadox, diethylcarbamizine, dimetridazole, diminazene, ivermectin, macrofilaricide, malathion, mitaban, oxamniquine, permethrin, praziquantel, prantel pamoate, selamectin, sodium stiboglucanate, thiabendazole, and combinations thereof, among others.

In other embodiments, medicants for treating otitis externa for use within the compositions disclosed herein include; ciprofloxacin and dexamethasone; neomycin and polymyxin B sulfates and hydrocortisone; acetic acid; hydrocortisone and acetic acid; ceftazidime; neomycin and hydrocortisone; acetic acid and aluminum acetate; colistin, hydrocortisone, neomycin, and thonzonium; and, combinations thereof, among others.

(II) Uses of Compositions

In various embodiments, the compositions disclosed herein comprise a formulation effective for treatment of excessive or impacted cerumen following administration to a subject in need. In other embodiments, the compositions disclosed herein comprise a formulation effective for prevention of excessive or impacted cerumen following administration to a subject in need.

A suitable subject includes a human, a livestock animal, a companion animal, a lab animal, or a zoological animal. In one embodiment, the subject may be a rodent, e.g., a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a specific embodiment, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

In various embodiments, a subject in need may have cerumen accumulation resulting in occlusion of one or more ear canals. As used herein, an "occlusion" refers to any amount of cerumen accumulation visible in the external auditory canal of the ear. In some embodiments, a subject in need may have cerumen accumulation resulting in at least 25%, at least 50%, at least 75% or at least 100% occlusion of one or more ear canals.

In other embodiments, a subject in need may have moderate to severe impacted cerumen. The severity of impacted cerumen may be determined by methods known in the field. As used herein, ears of a subject are assessed for severity of impacted cerumen by using an otoscope to visualize cerumen around tympanic membrane and subsequently grade the subject according to the scale provided in Table 1.

TABLE 1

| Grade | Severity | Percent Area Cerumen Around Tympanic Membrane | Description of Visualization |
|---|---|---|---|
| 1 | Normal | <3% | Normal and/or insignificant earwax present in ear canal. Tympanic membrane completely visible. |
| 2 | Minimal | 3-25% | Very little and mostly insignificant impacted cerumen that is not likely to have an effect on normal activities or cause any otologic or non-otologic symptoms; cerumen closer to the 25% impaction level may lead to increased impaction. Tympanic membrane is visible but still some minor presence of earwax. |
| 3 | Mild | 26-50% | Some excessive impacted cerumen causing partial occlusion of the ear canal usually causing some minor to major otological and/or non-otological symptoms at the 30-50% level. Tympanic membrane partially visible, but somewhat difficult to see. |
| 4 | Moderate | 51-75% | Moderate and excessive impacted cerumen causing partial occlusion of the ear canal causing major to serious complications in otological symptoms and in some cases, serious non-otological symptoms. Partial to very little of the tympanic membrane visible. |
| 5 | Severe | 76-100% | Severe and excessive impacted cerumen causing partial or complete occlusion of the ear canal; these subjects may have significant qualify of life issues with the complications from the otological and non-otological symptoms. Little if any of the tympanic membrane is visible. |

In other embodiments, a subject in need may have one or more symptoms associated with excessive or impacted human cerumen. In an aspect, symptoms associated with excessive or impacted human cerumen include occlusion of the ear canal, discomfort, decreased hearing, itching, otic fullness, ringing in the ears, hearing aid issues, otitis externa, vertigo, and tinnitus. In some aspects, a subject in need may have one or more symptoms associated with hearing aid issues. In other aspects, a hearing aid issue may be auditory feedback from hearing aid, damage to hearing aid, and pain and/or discomfort with hearing aid use.

In yet other embodiments, a subject in need may have been diagnosed with excessive or impacted human cerumen. In still other embodiments, a subject in need may exhibit one or more risk factors contributing to excessive or impacted human cerumen in one or more ear canals. Non-limiting examples of risk factors include narrow or not fully formed ear canals, hairy ear canals, increased age, recurring ear infections and impacted earwax, frequent use of in-ear headphones, stethoscopes, or other devices shown to compact cerumen in the ear canal. In an aspect, a subject in need may be genetically susceptible to excessive cerumen production. In another aspect, a subject in need may suffer from a condition and/or disease associated with excessive cerumen production. Non-limiting examples of conditions and diseases associated with excessive cerumen production include cancer, lupus, Sjögren's syndrome, osteomata, and certain skin conditions, such as eczema. In another aspect, a subject in need may use hearing aids in one or more ear canals.

(a) Treating cerumen accumulation

In various embodiments, compositions disclosed herein comprise a formulation effective for decreasing or eliminating cerumen production following administration to a subject. In some embodiments, compositions disclosed herein comprise a formulation effective for treating a partial or complete blockage of one or more ear canals. In some embodiments, compositions disclosed herein comprise a formulation effective for decreasing cerumen production at least 5%, at least 10%, at least 15%, at least 20%, at least 25%, at least 30%, at least 35%, at least 40%, at least 45%, or at least 50% following administration to a subject.

In other embodiments, compositions disclosed herein comprise a formulation effective for eliminating at least one, at least two, or at least three symptoms associated with ceruminosis following administration to a subject. In still other embodiments, compositions disclosed herein comprise a formulation effective for treating ceruminosis following administration to a subject.

(b) Preventing cerumen accumulation

In various embodiments, compositions disclosed herein comprise a formulation effective for preventing cerumen production following administration to a subject. In some embodiments, compositions disclosed herein comprise a formulation effective for preventing a partial or complete blockage of one or more ear canals. In some embodiments, compositions disclosed herein comprise a formulation effective for preventing cerumen production at least 5%, at least 10%, at least 15%, at least 20%, at least 25%, at least 30%, at least 35%, at least 40%, at least 45%, or at least 50% following administration to a subject.

In other embodiments, compositions disclosed herein comprise a formulation effective for preventing at least one, at least two, or at least three symptoms associated with ceruminosis following administration to a subject. In still other embodiments, compositions disclosed herein comprise a formulation effective for preventing ceruminosis following administration to a subject.

(III) Kits and Packaging of Compositions

In various embodiments, the present disclosure provides a kit comprising at least one or more compositions disclosed herein. In other embodiments, the present disclosure provides packaging comprising at least one or more compositions disclosed herein.

(a) Kits

The present disclosure may further comprise a kit, wherein the kit comprises at least a composition as described herein. In various embodiments, a kit may further comprise one or more additional compositions, instructions for applying the composition(s), instructions for complying with a suitable application regimen, an implement, a substrate, a delivery enhancement device, or combinations thereof. In some aspects, a kit may comprise an outer packaging unit, which in turn may comprise one or smaller, inner packaging units. In further aspects, inner packaging units may comprise one or more of individual components of the kit. In other aspects, inner and outer packaging units may be of any type suitable for containing, presenting and/or reasonably protecting from damage the contents of the kit. In still other aspects, inner packaging units may contain a quantity of a composition suitable for at least one dose, at least two doses, at least three doses, at least four doses, at least 5 doses, at least 6 doses, at least 7 doses, at least 8 doses, at least 9 doses, at least 10 doses, at least 11 doses, or at least 12 doses.

In various embodiments, a kit may further comprise instructions for methods of use. In some aspects, instructions to be provided with a kit may be in a fixed form. Non-limiting examples of fixed form instructions include written, recorded onto an audiocassette, videocassette, compact disc, or digital videodisc. In other aspects, a kit may comprise a notice in the form prescribed by a government agency regulating the manufacture, use or sale of pharmaceutical products, which notice reflects approval by the agency of manufacture, use of sale for human administration. In still other aspects, a kit may be labeled with information regarding mode of administration, sequence of administration, or the like. In other aspects, a kit may include means for reminding the subject to administer a composition. In other embodiments, a kit may further comprise a virtual package. As used herein, a "virtual package" refers to components of a kit that are associated by directions on one or more physical or virtual kit components instructing the user how to obtain the other components. A non-limiting example of a virtual package includes a bag or other container containing one component and directions instructing a subject to go to a website, contact a recorded message or a fax-back service, view a visual message, or contact a caregiver or instructor to obtain instructions on how to use the kit or safety or technical information about one or more components of a kit.

In other embodiments, a kit may be a single package. As used herein, the term "single package" means that the components of a kit are physically associated in or with one or more containers and considered a unit for manufacture, distribution, sale, or use. Examples of containers include, but are not limited to, bags, boxes, cartons, bottles, vials, syringes, test tubes, packages such as but not limited to shrink-wrap packages, stapled or otherwise affixed components, break-open or snap-open container or combinations thereof. In some aspects, a single package may comprise containers of compositions disclosed herein where the containers are formed from a variety of materials such as glass or plastic.

(b) Packaging

In various embodiments, compositions disclosed herein may be packaged. In some aspects, packaging of a composition may be for storage, shipment, display for sale, or a combination thereof. In various aspects, compositions may be packaged using one or more suitable materials known in the art. In other aspects, compositions may be packaged using one or more suitable methods known in the art. In some aspects, the choice of packaging material and/or packaging method is dependent on the dosage form of a composition disclosed herein to be packaged. Non-limiting examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

In some embodiments, compositions disclosed herein may be packaged wherein packaging increases the length of time a composition can be stored. As used herein, the "shelf-life" of a composition is the length of time after formulation that a composition can maintain one or more physiological effects following administration to a subject as detailed herein. In some aspects, compositions disclosed herein may be packaged wherein packaging increases the shelf-life of a composition by about 1 week, about 1 month, about 6 month, about 1 year, or about 2 years after formulation. In other embodiments, compositions disclosed herein may be packaged wherein packaging increases the length of time a composition can be stored at room temperature. As used herein, room temperature may be about 20° C. to about 25° C. In other embodiments, compositions disclosed herein may be packaged wherein packaging increases the length of time a composition can be stored at about 2° C. to about 40° C., about 10° C. to about 35° C., or about 20° C. to about 30° C. In some aspects, compositions disclosed herein may be packaged wherein packaging increases the length of time a composition can be stored at room temperature by about 1 week, about 1 month, about 6 month, about 1 year, or about 2 years.

In other embodiments, compositions disclosed herein may be packaged wherein the packaging allows for the packaged composition to be frozen. In some aspects, the packaging allows for the packaged composition to be frozen for about 1 week, about 1 month, about 6 month, about 1 year, or about 2 years. In still other embodiments, compositions disclosed herein may be packaged wherein the packaging allows for the packaged composition to be heated. In some aspects, the packaging allows for the packaged composition to shielded from light.

(IV) Methods of Using Compositions

Other aspects of the present invention are methods of administering compositions disclosed herein to a subject in need wherein administration modulates the production of cerumen and treats ceruminosis associated diseases, conditions or symptoms. Still other aspects of the present invention are methods of administering compositions disclosed herein to a subject in need wherein administration prevents cerumen production and diseases, conditions or symptoms associated with ceruminosis.

(a) Methods of Administration

In various embodiments, methods of administration of a composition disclosed herein may include local administration. As used herein the terms "local administration" or "locally administering" refers to direct administration of a composition at or to the vicinity of a site on or within a subject, at which site a biological effect of the composition is desired. In an aspect, methods of administration of a composition disclosed herein may include transdermal administration, subdermal administration, intradermal administration, subcutaneous administration, or a combination thereof. As used herein, "topical administration" refers to a type of local administration in which a composition disclosed herein may be applied to a subject's skin of the ear. In an aspect, a composition disclosed herein may be topically administered to the outer ear, middle ear, the inner ear, or a combination thereof. In another aspect, a composition disclosed herein may be topically administered to the outer ear. As used herein, the term "outer ear" refers to the portion of the ear including the pinna and the ear canal up to the eardrum. In still another aspect, a composition disclosed herein may be topically administered to least a portion of an ear canal of the subject.

In various embodiments, compositions disclosed herein may be administered by a delivery device capable of delivering the disclosed compositions onto the targeted area. In some embodiments, compositions disclosed herein may be administered by syringing. In an aspect, the delivery system is a syringe and needle apparatus that is capable of unloading the compositions or formulations disclosed herein onto the surface of the outer ear, middle ear, the inner ear, or a combination thereof. In other embodiments, compositions disclosed herein may be administered onto the surface of the outer ear, middle ear, the inner ear, or a combination thereof by using a dropper.

Regardless of the cause and/or circumstance resulting in the excess secretion and/or build-up of cerumen—often before the methods described herein can be performed— existing cerumen should be removed from the subject's ear canal. There are several methods known in the art for removing cerumen from the ear canal; including, but not limited to irrigation, hydrating the ear canal, use of a curette or similar device, mineral oils, binocular microscopes, microprobes, suction, and/or combinations thereof. In some aspects, irrigation can be used to remove cerumen from the subject's ear canal. In other aspects, irrigation can be performed with water, one or more alcohols, boric acid, acetic acid, or a combination thereof. Importantly, the removal of cerumen, especially excess cerumen, by someone other than a skilled medical professional is not advised as the condition could be worsened, leading to infection or puncture of the eardrum, all of which can lead to serious complications.

Methods of administration to the ear canal of a subject can include virtually any method of local administration known to those of ordinary skill in the art. In one embodiment, the muscarinic antagonist may be delivered topically to the ear canal of a subject. In another embodiment, compositions disclosed herein can be delivered subdermally to the ear canal of a subject. In yet another embodiment, compositions disclosed herein can be delivered intradermally to the ear canal of a subject. In another embodiment compositions disclosed herein can be delivered via extended release injection or a slow release implant to the ear canal of a subject. Exemplary implants are described in U.S. Pat. Nos. 6,306,423, and 6,312,708, which are incorporated by reference.

In some embodiments, a hearing aid may be coated or impregnated with compositions disclosed herein prior to insertion of hearing aid. In other embodiments, compositions disclosed herein can be formulated for controlled release from hearing aid wax guards. In still other embodiments, compositions disclosed herein can be formulated for controlled release from hearing aid.

In one embodiment, compositions disclosed herein can be administered transdermally. In certain embodiments wherein compositions disclosed herein are administered transdermally, an enhancing agent can be used to enhance the permeability of the skin thereby allowing the bioactive muscarinic antagonist to act at a desired target structure. An enhancing agent used in combination with the muscarinic antagonist in the pharmaceutical composition can be a DMSO or non-DMSO based enhancing agent. The enhancing agent preferably does not injure the skin, and more preferably, temporarily permeabilizes the skin so that once the muscarinic antagonist has been delivered through the skin, the skin reduces its permeability to other factors. As an example, Catz et al., in U.S. Pat. No. 5,238,933 (herein incorporated by reference), discloses skin permeation enhancer systems that increase the permeability of the skin to transdermally administered, muscarinic antagonists. A list of additional enhancing agents is given above.

Compositions disclosed herein can be administered in a single administration or it can be administered on the basis of one to several times every day, week, or month. One to several times daily, weekly, biweekly, monthly, semimonthly, bimonthly, quarterly, semiannual and/or annual administration may also be suitable to provide the desired beneficial clinical response. The composition can be administered every few days, weeks or months. The muscarinic antagonists can also be administered every other day, week or month. In some specific embodiments, the muscarinic antagonist composition is administered once or twice daily, and in other embodiments, the muscarinic antagonist composition is administered once or twice weekly.

If an applicator is required in order to administer a composition disclosed herein, the applicator can be adapted for otic use. Suitable exemplary applicators include, but are not limited to, swab, syringes, bulbs, spray bottles, dropper bottles, and other like applicators. Compositions disclosed herein can be administered by placing said composition on the applicator and using the applicator to transfer a unit dose to the ear canal of a subject.

In some embodiments, a physician may have to alter dosage of a composition disclosed herein in each case (i.e. subject) in accordance with the assessment of the severity of the condition, as typically done when treating subjects with a condition/disorder. Further, in some embodiments, the administration of a composition as disclosed herein may have to be repeated at least one additional time, in some cases several times, depending on the severity of the condition and the subject's overall health. If, for example, a subject is not deemed physically suitable for a full administration of the muscarinic antagonist, or if a full administration is not desired for any reason, smaller doses on multiple occasions may prove to be efficacious. Further still, if a composition is administered at a certain dosage that is not sufficient to attain the desired treatment goal, such as reduction in an amount of ear wax produced over a particular time period, the dose may be increased for a second and subsequent administration session(s) by the attending physical as he/she sees fit.

In another embodiment, compositions disclosed herein can be associated with a prosthesis that can be placed in the ear canal of a subject, where the prosthesis slowly releases one or more muscarinic antagonists into the skin of the ear canal. In one embodiment, the prosthesis assumes the shape of the outer ear. In other embodiments, compositions disclosed herein can be impregnated into a polymer matrix associated with or disposed upon the surface of the prosthesis or can be impregnated into the prosthesis itself. In some aspects, the polymer or prosthesis can be tailored to release one or more muscarinic antagonists over a predetermined amount of time. In other aspects, the prosthesis can further comprise an enhancing agent.

Non-chemical methods of enhancing muscarinic antagonist release in subdermal structures may include steps of disrupting the stratum corneum to reduce the impermeability of the stratum corneum, and applying a muscarinic antagonist to the skin location in which the stratum corneum has been disrupted. Disrupting the stratum corneum refers to either completely removing the stratum corneum from a region of a subject's skin, such as in an ear canal, or partially removing portions of the stratum corneum at a location on the subject's skin so that relatively small stratum corneum-free regions of skin are present. The skin may be disrupted using any suitable method without imparting significant pain to the subject. In preferred embodiments of the methods, the stratum corneum is non-chemically disrupted. For example, the stratum corneum may be abrasively scrubbed to disrupt the laminar barrier of the stratum corneum. Or, the stratum corneum may be disrupted by applying an adhesive, such as adhesive tape or wax, to the skin, and subsequently removing the adhesive from the skin. Because such methods of disrupting the stratum corneum may cause some pain, it may be desirable to provide a topical anesthetic to the skin, such as lidocaine cream, to temporarily reduce any pain that may be caused by the disruption. These methods require a skilled medical professional because the skin lining the ear canal is very sensitive, a very compact area, and the procedures may be uncomfortable for a subject.

Additional transdermal methods that non-chemically enhance the skin's permeability include low frequency electrolysis (20 KHz to 1 MHZ). Electrolysis is defined as the passing of a direct electric current through an ionic substance that is either molten or dissolved in a suitable solvent, producing chemical reactions at the electrodes and a decomposition of the materials. Low frequency electrolysis, as used herein, refers to electrolysis at a frequency that is less than 1 MHZ, and preferably in the range of 20 KHz to 40 kHz. Electrolysis is delivered in pulses, for example, 100 msec pulses at a frequency of 1 Hz. The intensity of the electrolysis may vary between 0) and 1 W/cm$^2$, and frequently varies between 12.5 mW/cm$^2$ and 225 mW/cm$^2$. Typical duration of exposure to electrolysis is between about 1 and about 10 minutes. Electrolysis is applied without causing an increase in skin temperature greater than about 1 degree Celsius. Low frequency electrolysis may be used alone or in combination with the composition to improve the permeability of the skin to the muscarinic antagonist. Examples of electrolysis techniques for improving skin permeability may be found in U.S. Pat. Nos. 6,002,961 and 5,814,599, hereby incorporated by reference.

It has been discovered that low frequency electrolysis temporarily disrupts the stratum corneum so that subsequent topical application of, e.g., a muscarinic antagonist achieves a therapeutic effect. In other words, the disruption caused by the electrolysis persists for several minutes, for example between about 10 and 30 minutes, to provide relatively easy transdermal delivery of muscarinic antagonist to the subject. After about 30 minutes, the stratum corneum begins to resume its natural structure, and the permeability of the stratum corneum temporally decreases. Thus, one method of the invention, includes the step of applying low frequency electrolysis to one or more regions of the ear canal skin, and subsequently topically applying muscarinic antagonist to those regions of the skin that were exposed to the low frequency electrolysis, where the muscarinic antagonist is provided in a composition containing an enhancing agent, which facilitates penetration of the muscarinic antagonist to the subject.

In various embodiments, compositions administered as disclosed herein may comprise a therapeutically effective amount of one or more muscarinic antagonists. As used herein, the term "therapeutically effective" refers to an amount of an administered muscarinic antagonist that reduces or ameliorates a condition or symptom in frequency and/or intensity resulting from excessive secretion and/or build-up of cerumen in the ear canal of a subject. A therapeutically effective amount of muscarinic antagonist delivered to a subject may be an amount that does not result in undesirable systemic side effects, but results in a reduction in cerumen secretion and impacts problems associated with excess cerumen, such as hearing loss and pain. In various embodiments, compositions administered disclosed herein may comprise about 0.005% to about 15%, about 0.01% to about 14%, or about 0.02% to about 10% total muscarinic antagonist compound by total weight of the composition. In other embodiments, compositions administered as disclosed herein may comprise about 0.005%, about 0.01%, about 0.05%, about 0).1%, about 0.2%, about 0.5%, about 1%, about 5%, about 10%, or about 15% total muscarinic antagonist compound by total weight of the composition.

(b) Frequency of Administration

In some embodiments, a composition disclosed herein may be administered to a subject in need thereof once. In some embodiments, a composition disclosed herein may be administered to a subject in need thereof more than once. In some embodiments, a first administration of a composition disclosed herein may be followed by a second administration of a composition disclosed herein. In some embodiments, a first administration of a composition disclosed herein may be followed by a second and third administration of a composition disclosed herein. In some embodiments, a first administration of a composition disclosed herein may be followed by a second, third, and fourth administration of a composition disclosed herein. In some embodiments, a first administration of a composition disclosed herein may be followed by a second, third, fourth, and fifth administration of a composition disclosed herein.

The number of times a composition may be administered to an subject in need thereof can depend on the discretion of a medical professional, the disorder, the severity of the disorder, and the subject's response to the formulation. In some embodiments, a composition disclosed herein may be administered once to a subject in need thereof with a mild acute condition. In some embodiments, a composition disclosed herein may be administered more than once to a subject in need thereof with a moderate or severe acute condition. In some embodiments, a composition disclosed herein may be administered for an extended period of time to a subject in need thereof with a chronic condition. In some embodiments, a composition disclosed herein may be administered continuously; alternatively, the dose of drug being administered may be temporarily reduced or temporarily suspended for a certain length of time (i.e., a "drug holiday"). In an aspect, the length of the drug holiday can vary between 2 days and 1 year, including by way of example only, 2 days, 1 week, 1 month, 6 months, and 1 year. In another aspect, dose reduction during a drug holiday may be from 10%-100%, including by way of example only 10%, 25%, 50%, 75%, and 100%.

In an aspect, the desired daily dose of compositions disclosed herein may be presented in a single dose or as divided doses administered simultaneously (or over a short period of time) or at appropriate intervals. In various embodiments, administration of a composition disclosed herein may be administered to a subject about once a day, about twice a day, about three times a day. In other embodiments, administration of a composition disclosed herein may be administered to a subject at least once a day, at least once a day for about 2 days, at least once a day for about 3 days, at least once a day for about 4 days, at least once a day for about 5 days, at least once a day for about 6 days, at least once a day for about 1 week, at least once a day for about 2 weeks, at least once a day for about 3 weeks, at least once a day for about 4 weeks, at least once a day for about 8 weeks, at least once a day for about 12 weeks, at least once a day for about 16 weeks, at least once a day for about 24 weeks, at least once a day for about 52 weeks and thereafter. In a preferred embodiment, administration of a composition disclosed herein may be administered to a subject once a day for at about 4 weeks.

In other embodiments, administration of a composition disclosed herein may be administered to a subject at least once a week, at least once a week for about 2 weeks, at least once a week for about 3 weeks, at least once a week for about 4 weeks, at least once a week for about 8 weeks, at least once a week for about 12 weeks, at least once a week for about 16 weeks, at least once a week for about 24 weeks, at least once a week for about 52 weeks and thereafter. In a preferred embodiment, administration of a composition disclosed herein may be administered to a subject once a week for at about 12 weeks.

In various embodiments, methods of administration disclosed herein increase subject compliance of administration of a composition disclosed herein. As used herein, the term "subject compliance" refers to the frequency to which a subject correctly follows administration of compositions disclosed herein. In some aspects, methods of administration disclosed herein increase subject compliance by about 1% to about 100%, about 5% to about 95%, or about 10% to about 90%.

In various embodiments, the amount and/or frequency of compositions disclosed herein administered can be adjusted based upon factors such as the particular compound, disease condition and its severity, according to the particular circumstances surrounding the case, including, e.g., the route of administration, the condition being treated, the target area being treated, and the subject or host being treated. For some subjects, a single otic administration of the muscarinic antagonist is sufficient to at least reduce the rate of formulation and/or accumulation of cerumen for a period of one to four or more weeks. For other subjects, regular periodic otic administration of the muscarinic antagonist is required. For subjects with competitive outstanding physiologies, poor overall health, and/or hygiene, more frequent administration and/or administration of more concentrated compositions may be required. Subjects taking other medications that counteract the action of muscarinic antagonists may also require more frequent administration and/or administration of more concentrated compositions.

In some embodiments, a composition as disclosed may be initially administered followed by a subsequent administration of one for more different formulations or treatment regimens. In other embodiments, a composition as disclosed may be administered after administration of one for more different formulations or treatment regimens. Some embodiments of the methods of the invention further comprise the step of irrigating the ear canal of the subject, and some embodiments further comprise the step of administering an antibiotic to the ear canal. Also, some embodiments further comprise the step of administering an anesthetic to the ear canal.

(c) Methods of Treating Cerumen Accumulation

In various embodiments, administration of compositions disclosed herein decreases or eliminates cerumen production following administration to a subject. The clinical response to the muscarinic antagonist composition may vary depending upon a subject's age, gender, overall health, hygiene, outstanding pathologies, specific muscarinic antagonist(s) administered, the amount(s) in which it is (they are) administered, and/or the specific formulation that is administered. For some subjects, a single otic administration of the muscarinic antagonist compound is sufficient to at least reduce the rate of formulation and/or accumulation of cerumen for a period of one to four or more weeks. For other subjects, regular periodic otic administration of the muscarinic antagonist compound is required. For subjects with competitive outstanding physiologies, poor overall health, and/or hygiene, more frequent administration and/or administration of more concentrated compositions may be required. Subjects taking other medications that counteract the action of muscarinic antagonists may also require more frequent administration and/or administration of more concentrated compositions. In some embodiments, administration of compositions disclosed treats a partial or complete blockage of one or more ear canals. In some embodiments, administration of compositions disclosed herein decreases cerumen production at least 5%, at least 10%, at least 15%, at least 20%, at least 25%, at least 30%, at least 35%, at least 40%, at least 45%, or at least 50% following administration to a subject.

In other embodiments, administration of compositions disclosed herein eliminates at least one, at least two, or at least three symptoms signs, symptoms or complications of excessive or impacted human cerumen. In an aspect, administration of compositions disclosed herein eliminates at least one sign, symptom or complication of excessive or impacted human cerumen including occlusion of the ear canal, discomfort, decreased hearing, itching, otic fullness, ringing in the ears, hearing aid faults, otitis externa, vertigo, and tinnitus. In some aspects administration of compositions disclosed herein eliminates hearing aid issues. In other aspects, a hearing aid issue may be auditory feedback from hearing aid, damage to hearing aid, and pain and/or discomfort with hearing aid use.

In various embodiments, administration of compositions disclosed herein alleviates excessive or impacted human cerumen-associated pain. As used herein, the term "alleviate" as applied to excessive or impacted human cerumen-associated pain refers to a reduction of excessive or impacted human cerumen-associated pain in a subject after treatment with a disclosed composition relative to before treatment. In some embodiments, excessive or impacted human cerumen-associated pain can be reduced by more than 25%. In some embodiments, excessive or impacted human cerumen-associated pain may be reduced by more than 50%. In some embodiments, the reduction of excessive or impacted human cerumen-associated pain may be more than 75%.

In other embodiments, administration of compositions disclosed herein improves excessive or impacted human cerumen-associated hearing loss. As used herein, the term "improve" as applied to excessive or impacted human cerumen-associated hearing loss refers to a measured improvement of hearing in a subject after treatment with a disclosed composition relative to before treatment. In some embodiments, excessive or impacted human cerumen-associated hearing loss is improved by more than 25%. In some embodiments, excessive or impacted human cerumen-associated hearing loss is improved by more than 50%. In some embodiments, excessive or impacted human cerumen-associated hearing loss is improved by more than 75%.

In other embodiments, administration of compositions disclosed herein improves quality of life for a subject. As used herein, the term "quality of life" refers to the degree of physical wellbeing achieved in everyday life. When a subject is physically well, that subject has a high quality of life. In contrast, when a subject experiences physical pain from cerumen accumulation and/or hearing loss, that subject has a low quality of life. In some aspects, administration of compositions disclosed herein improves quality of life by about 1% to about 100%, about 10% to about 90%, or about 20% to about 80% for a subject.

(d) Methods of Preventing Cerumen Accumulation

In various embodiments, administration of compositions disclosed herein prevents cerumen production following administration to a subject. The clinical response to the muscarinic antagonist composition may vary depending upon a subject's age, gender, overall health, hygiene, outstanding pathologies, specific muscarinic antagonist(s) administered, the amount(s) in which it is (they are) administered, and/or the specific formulation that is administered. For some subjects, a single otic administration of the muscarinic antagonist is sufficient to at least reduce the rate of formulation and/or accumulation of cerumen for a period of one to four or more weeks. For other subjects, regular periodic otic administration of the muscarinic antagonist is required. For subjects with competitive outstanding physiologies, poor overall health, and/or hygiene, more frequent administration and/or administration of more concentrated compositions may be required. Subjects taking other medications that counteract the action of muscarinic antagonists may also require more frequent administration and/or administration of more concentrated compositions. In some embodiments, administration of compositions disclosed herein prevents a partial or complete blockage of one or more ear canals. In some embodiments, administration of compositions disclosed herein prevents cerumen production at least 5%, at least 10%, at least 15%, at least 20%, at least 25%, at least 30%, at least 35%, at least 40%, at least 45%, or at least 50% following administration to a subject.

In other embodiments, administration of compositions disclosed herein prevents at least one, at least two, or at least three symptoms signs, symptoms or complications of excessive or impacted human cerumen. In an aspect, administration of compositions disclosed herein prevents at least one sign, symptom or complication of excessive or impacted human cerumen including occlusion of the ear canal, discomfort, decreased hearing, itching, otic fullness, ringing in the ears, hearing aid faults, otitis externa, vertigo, and tinnitus. In some aspects administration of compositions disclosed herein prevents hearing aid issues. In other aspects, a hearing aid issue may be auditory feedback from hearing aid, damage to hearing aid, and pain and/or discomfort with hearing aid use.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Preparation of Muscarinic Antagonist Compositions

The following process was used to make a liquid formulation for topical administration of the ear to treat and/or prevent excessive or impacted cerumen. Methylscopolamine bromide (0.06 mg) was dissolved in 9.95 mL dimethyl sulfoxide (DMSO) at room temperature (21° C.±3° C.). After methylscopolamine bromide was completely dissolved in DMSO, 3 ml of the methylscopolamine bromide/DMSO solution was mixed with 27 ml of propylene glycol until a homogenous mixture was achieved. The resulting formulation contained 0.01% w/v methscopolamine bromide in solution. Further, the final formulation was 30 ml total volume and had the native viscosity of propylene glycol with a pH of about 7. The 0.01% w/v methscopolamine bromide solution (30 ml) was stored in a light-proof, child-proof amber glass bottle at room temperature (21° C.±3° C.) for up to 4 months without a decrease in efficacy.

Following a similar process, other liquid formulations were prepared as shown in table 2, provided below;

TABLE 2

| Liquid Formulations | |
| --- | --- |
| Active Formulation Name | Active Formulation Components |
| A | 1% Methylscopolamine bromide 99% DMSO |
| A2 | 1% Methylscopolamine bromide 10% DMSO 89% propylene glycol |
| A3 | 8% Methylscopolamine bromide 2% DMSO 90% propylene glycol |
| A4 | 4% Methylscopolamine bromide 6% DMSO 90% propylene glycol |
| C3 | 0.02% Scopolamine hydrobromide 99.98% Propylene glycol |
| Control Solution Name | Control Solution Components |
| B | 100% DMSO |
| B2 | 10% DMSO 90% Propylene glycol |

Formulations were administered to one ear designated as treated ear with other ear serving as control with no treatment. Ears observed monthly for minimum of 6 months. Then the ears were switched with previous control ear serving as the treated ear and vice versa for a minimum of 6 months.

Next, different formulation was then used in one ear and a different concentration of a similar formulation in the opposite ear. After monthly observation for 6 months, the ears were switched.

Also tested effects of carrier agents B and B2 in control ear as compared to active ingredient formulations applied to designated treated ear for minimum of 6 months. After monthly observation for a minimum of 6 months, the ears were switched.

Example 2. Daily Administration of 0.01% w/v Methscopolamine Solution Prevented Excessive Accumulation of Cerumen Subjects in need of preventive therapy for excessive or impacted cerumen were identified for participation in the pilot study. Subjects in need of preventive therapy were identified as those who required repeated cerumen removals every six weeks to every three months over the course of at least one year. Subjects that met the above criteria could not also present any of the following co-occurring pathologies; tympanic membrane perforations, infection, cholesteatoma, mastoid cavities, and other abnormalities of the external ear. The use of hearing aids was allowed as needed during the study and was not a restricting factor when selecting study participants.

Figure 1B:
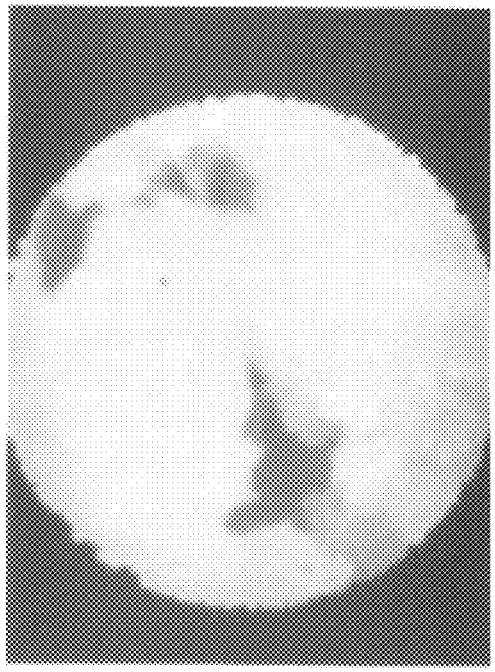
FIG. 1B depicts an image of a subject's right ear that was not cleaned for 6 months resulting in excessive wax accumulation which blocked complete visualization of tympanic membrane.

Four subjects that met the study criteria were selected for the study. FIG. 1A and FIG. 1B depicts a representative images of the left and right ears, respectively, of a subject selected for the study. The subject presented with excessive cerumen accumulation in both ears, preventing complete visualization of tympanic membrane (FIG. 1A and FIG. 1B). Six months prior to this image, the subject's ears where cleared of all cerumen.

Figure 2:
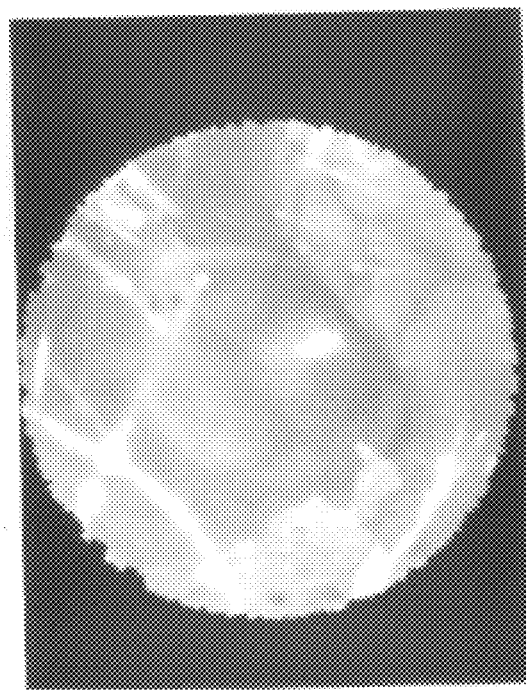
FIG. 2 depicts an image of the right ear of a subject immediately after excessive cerumen was removed from the external ear canal mechanically.

All cerumen and debris was removed from the external ear canals of each subject mechanically. Immediately following irrigation, the cleaned external ear canals were photographed to document the study baseline (FIG. 2).

Figure 3B:
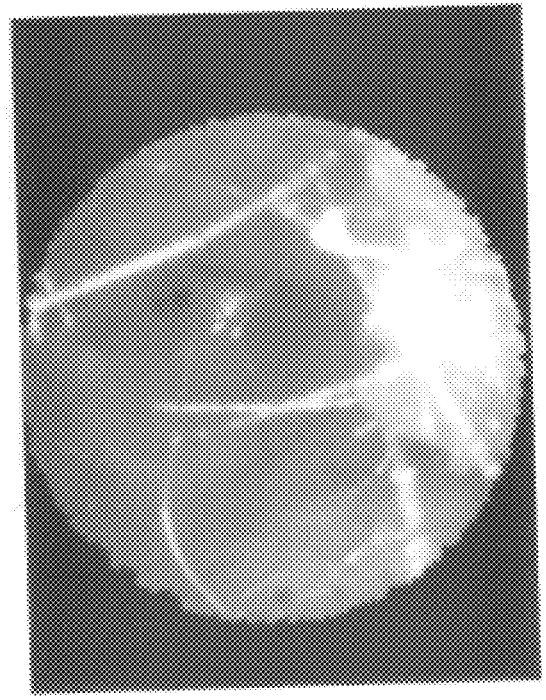
FIG. 3B depicts an image of a subject's right ear that was not treated for 6 weeks after removing all wax and debris.
Figure 3A:
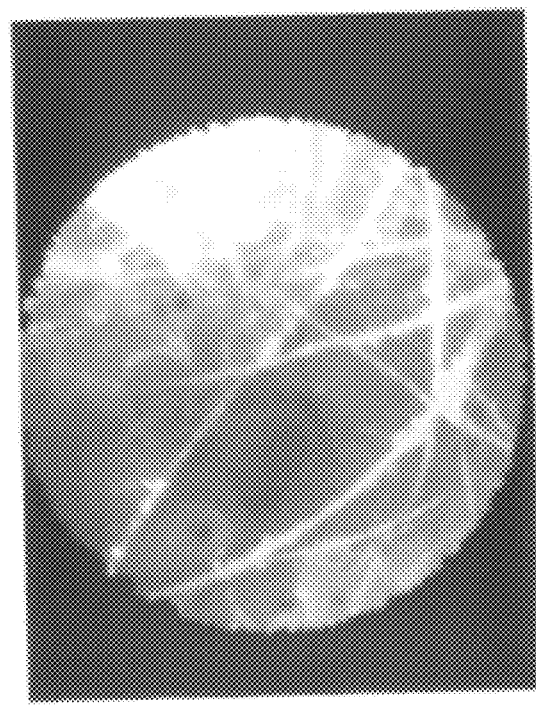
FIG. 3A depicts an image of a subject's left ear that had not treated for 6 weeks after removing all wax and debris.

Both ears of the subjects remained untreated for 6 weeks. After six weeks, the external ear canals were photographed (FIG. 3A and FIG. 3B). Photographs demonstrated the presence of wax accumulation in each ear, partially occluding visualization of the tympanic membrane (FIG. 3A and FIG. 3B).

Each subject was instructed to dispense 3 drops of 0.01% w/v methscopolamine solution (0).15 ml total volume) onto a cotton swab and then gently insert the cotton swab into one ear's external auditory canal to self-administer the 0.01% w/v methscopolamine solution once a day. For the opposite ear, each subject was instructed to dispense 3 drops of propylene glycol (0.15 ml total volume) onto a cotton swab and then gently insert the cotton swab into the opposite ear's external auditory canal once a day congruent with self-administration of the 0.01% w/v methscopolamine solution.

After 4 weeks of daily administration of 0.01% w/v methscopolamine solution, each of the four subjects presented with less than 5% of the external auditory canal occluded with cerumen in the methscopolamine-treated ear canal. Two of the four subjects did not have any cerumen accumulation. After 4 weeks of daily administration of propylene glycol, each of the four subjects presented with least 80% of the external auditory canal occluded with cerumen in the vehicle-treated ear canal.

Figure 4B:
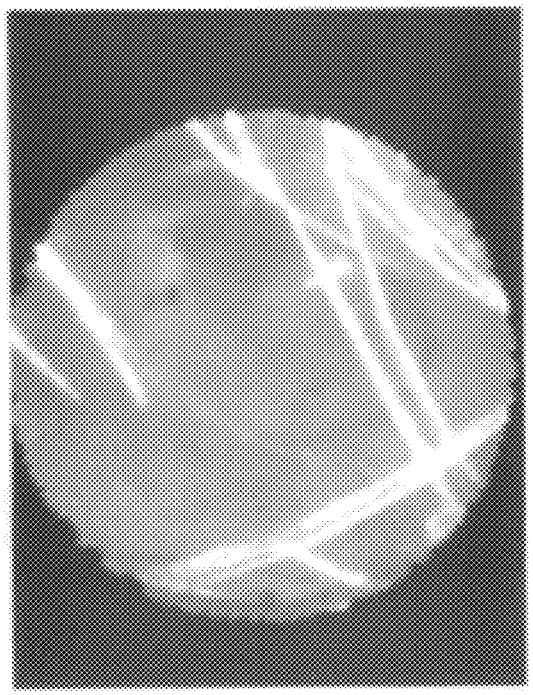
FIG. 4B depicts an image of a subject's right ear after 4 months of daily administration of 0.01% w/v methscopolamine solution.
Figure 4A:
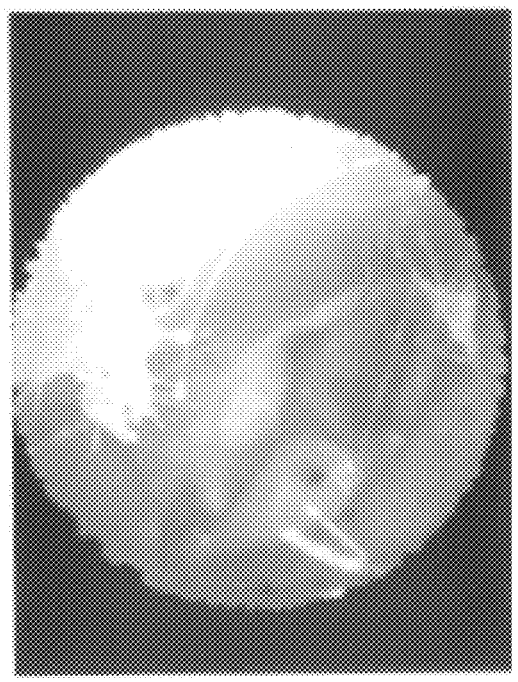
FIG. 4A depicts an image of a subject's left ear after 4 months of daily administration of propylene glycol (vehicle control).

One of the four subjects continued to administer 0.01% w/v methscopolamine solution to one ear daily for an additional 3 months. After a total of 4 months of methscopolamine treatment, the subject's treated ear (right ear) did not have any cerumen accumulation (FIG. 4B). However, the external auditory canal of the subject's untreated ear (left ear) was 50% occluded with cerumen (FIG. 4A).

Results from this study show that daily administration of 0.01% w/v methscopolamine solution is effective for the prevention of excessive cerumen accumulation for at least four weeks in subjects that require frequent cerumen removal. In addition, the benefits of daily administration of 0.01% w/v methscopolamine solution can be observed for at least 4 months of continued administration.

Example 3. Daily Administration of 0.01% w/v Methscopolamine Solution Reduces Excessive Accumulation of Cerumen A subject with about 50% of the external auditory canal occluded with cerumen in one ear self-administered a 0.01% w/v methscopolamine solution once a day for seven weeks. Specifically, the subject dispensed 3 drops of 0.01% w/v methscopolamine solution (0).15 ml total volume) onto a cotton swab and then gently inserted the cotton swab into the affected ear's external auditory canal to self-administer the 0.01% w/v methscopolamine solution once a day. After seven weeks of daily administration of 0.01% w/v methscopolamine solution, the treated ear had less than 5% of the external auditory canal occluded with cerumen.

The subject continued to self-administer the 0.01% w/v methscopolamine solution once a day for an additional 3 months. After the 3 months, the treated ear had less than 5% of the external auditory canal occluded with cerumen.

Results from this study show that daily administration of 0.01% w/v methscopolamine solution is effective at reducing excessive cerumen accumulation within seven weeks and prevents the return of excessive cerumen accumulation for up to 3 months after continued daily administration of 0.01% w/v methscopolamine solution.

Example 4; Weekly Administration of 0.01% w/v Methscopolamine Solution Controls Cerumen Accumulation Over Time Two subjects in need of preventive therapy to control excessive accumulation of cerumen over an extensive period of time were selected for the study. All cerumen and debris was removed from the external ear canals of each subject by irrigation. Immediately following irrigation, the cleaned external ear canals were photographed to document the study baseline. The two subjects were instructed to dispense 3 drops of 0.01% w/v methscopolamine solution (0).15 ml total volume) onto a cotton swab and then gently insert the cotton swab into the ear's external auditory canal to self-administer the 0.01% w/v methscopolamine solution once a week for four months.

After 4 months of weekly administration of 0.01% w/v methscopolamine solution, each of the two subjects presented with less than 5% of the external auditory canal occluded with cerumen.

Results from this study show that weekly administration of 0.01% w/v methscopolamine solution is effective at controlling excessive cerumen accumulation for up to 4 months in subjects that require prevention of cerumen accumulation for extended time periods.

Example 5; Daily Administration of 0.01% w/v Methscopolamine Solution Prevents Cerumen Impactions Caused by Hearing Aid Use A subject with hearing aids inserted into both ears required removal of cerumen impactions every three to six months. Before administration of the 0.01% w/v methscopolamine solution, all cerumen and debris was removed from the external ear canals by irrigation. Immediately following irrigation, the cleaned external ear canals were photographed to document the study baseline. The subject was then instructed to dispense 3 drops of 0.01% w/v methscopolamine solution (0).15 ml total volume) onto a cotton swab and then gently insert the cotton swab into each ear's external auditory canal to self-administer the 0.01% w/v methscopolamine solution once a day for eight weeks. The subject continued to wear hearing aids in the treated ears for the duration of the study. After eight weeks of daily 0.01% w/v methscopolamine solution administration while using hearing aids, the subject did not have a cerumen impaction in either ear.

The study of this subject demonstrated that daily administration of a 0.01% w/v methscopolamine solution prevented the formation of cerumen impactions that are commonly observed as a consequence of hear aid use. Additionally, the study shows that application of a 0.01% w/v methscopolamine solution can coincide with hearing aid use without loss of methscopolamine efficacy.

Example 6. Administration of 0.01% w/v Methscopolamine Solution Prevents Symptoms and Complications of Excessive or Impacted Human Cerumen A subject required cerumen removal every three to six months to resolve hearing loss and the occasional otitis externa associated with excessive or impacted human cerumen. The subject was instructed to dispense 3 drops of 0.01% w/v methscopolamine solution (0).15 ml total volume) onto a cotton swab and then gently insert the cotton swab into each ear's external auditory canal to self-administer the 0.01% w/v methscopolamine solution once a day for 4 weeks. After 4 weeks of daily 0.01% w/v methscopolamine solution administration, the subject did not report any hearing loss or difficulty hearing resulting from cerumen accumulation. Also the subject did not present with any symptoms of cerumen-induced otitis externa.

The subject was then instructed to dispense 3 drops of 0.01% w/v methscopolamine solution (0).15 ml total volume) onto a cotton swab and then gently insert the cotton swab into the affected ear's external auditory canal to self-administer the 0.01% w/v methscopolamine solution once a week for 4 months. After 4 months of weekly 0.01% w/v methscopolamine solution administration, the subject did not report any hearing loss or difficulty hearing resulting from cerumen accumulation. Also the subject did not present with any symptoms of cerumen-induced otitis externa.

These observations demonstrate that administration of a 0.01% w/v methscopolamine solution to the ear of subject that frequently presents with symptoms and/or complications of excessive or impacted human cerumen can prevent future presentation of said symptoms.

Example 6. Daily Administration of Formulations a, A2, A3, A4 or C3 Prevented Excessive Accumulation of Cerumen Subjects in need of preventive therapy for excessive or impacted cerumen were identified for participation in the pilot study. Subjects in need of preventive therapy were identified as those with cerumen accumulation resulting in 75% to 100% occlusion of one or more ear canals, or who required repeated cerumen removals every six weeks to every three months over the course of at least one year. Subjects that met the above criteria could not also present any of the following co-occurring pathologies; tympanic membrane perforations, infection, cholesteatoma, mastoid cavities, and other abnormalities of the external ear. The use of hearing aids was allowed as needed during the study and was not a restricting factor when selecting study participants.

All cerumen and debris was removed from the external ear canals of each subject mechanically. Immediately following irrigation, the cleaned external ear canals were photographed to document the study baseline. Subjects were selected at random to apply either formulation A, A2, A3, A4, or C3 to one ear and apply DMSO to the opposite ear every day for 6 months. Each subject was instructed to dispense 3 drops of assigned formulation (0.15 ml total volume) onto a cotton swab and then gently insert the cotton swab into one ear's external auditory canal to self-administer the formulation once a day. For the opposite ear, each subject was instructed to dispense 3 drops of DMSO (0.15 ml total volume) onto a cotton swab and then gently insert the cotton swab into the opposite ear's external auditory canal once a day congruent with self-administration of the assigned formulation.

About 10% of study participants ended the treatment regimen at 3 months due to issues unrelated to formulation use (i.e., dermatitis, scleropathy). Examination of these patients at 3 months showed that cerumen accumulation was reduced to occluding less 50% of the treated ear canals.

Remaining study participants were examined at 6 months. For all formulations used, average cerumen accumulation occluded less than 25% of the treated ear canals. Subjects reported otological symptoms were less in the treated ear compared to the ear receiving DMSO alone after the 6 month trial. About 90% of subjects reported that the feelings of fullness, itching, and irritation in the untreated ear was not present in the treated ear. Of the subjects who completed the study for 6 months, all reported satisfaction with the application process in terms of frequency or administration and outcome.

What is claimed:

1. A liquid composition for the treatment and/or prevention of excessive cerumen, comprising;
   a compound or pharmaceutically acceptable prodrug or salt thereof, wherein the compound or a combination thereof is selected from the group consisting of

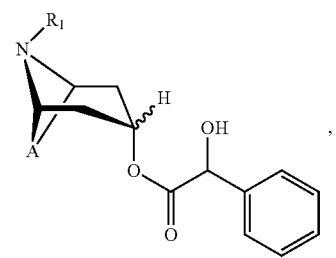

I

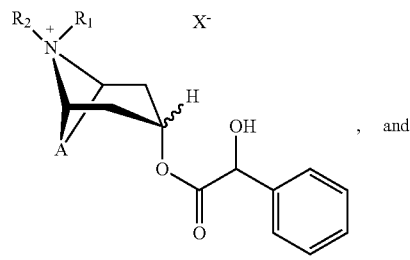

II, and

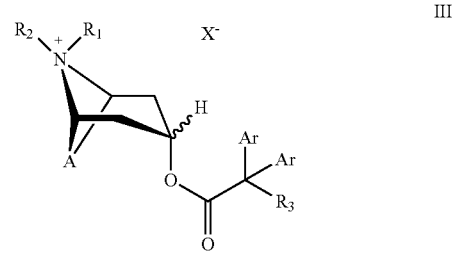

III wherein A is a group selected from

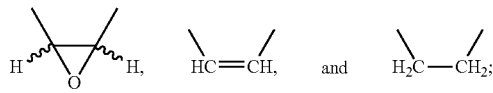

R¹ and R² are each independently hydrogen, $C_1$-$C_4$-alkyl optionally substituted with hydroxy or halogen;

R³ is hydroxy, $C_1$-$C_4$-alkyl, $C_1$-$C_4$-alkoxy, $CF_3$, or fluorine;

X⁻ denotes an anion selected from among chlorine, bromine, iodine, methanesulphonate or trifluoromethanesulphonate; and Ar is phenyl, naphthyl, thienyl, and furyl, each optionally mono- or disubstituted with one or two groups selected from $C_1$-$C_4$-alkyl, $C_1$-$C_4$-alkoxy, hydroxy, fluorine, chlorine, bromine, or $CF_3$;

wherein the compound is present in a total amount of 0.005% to 15% by weight of the liquid composition;

an otologically acceptable topical carrier, wherein the otologically acceptable topical carrier is propylene glycol and, wherein the otologically acceptable topical carrier is present in an amount of about 50% to about 99.995% by weight of the liquid composition; and wherein the liquid composition is formulated for topical administration to the external ear canal.

2. The liquid composition of claim 1 wherein the otic liquid composition comprises one or more pharmaceutically active agents selected from the group consisting of antibacterial agents, anti-viral agents, anti-fungal agents, disinfectant agents, analgesic agents, immuno-suppressive agents, permeability agents, and premedication agents.

3. The liquid composition for the treatment and/or prevention of excessive cerumen, comprising;

a compound or pharmaceutically acceptable prodrug or salt thereof, wherein the compound or a combination thereof is selected from the group consisting of formula IIa;

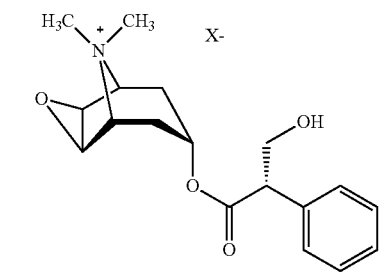

wherein

X⁻ denotes an anion selected from among chlorine, bromine, iodine, methanesulphonate or trifluoromethanesulphonate, formula IIb;

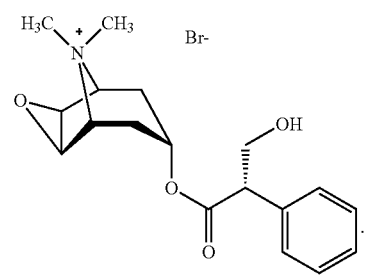

and formula Ia

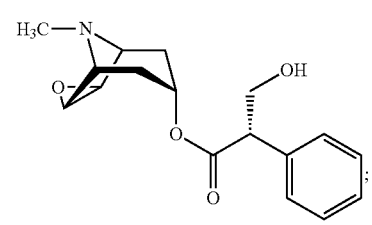

wherein the compound is present in a total amount of 0.005% to 15% by weight of the liquid composition;

an otologically acceptable topical carrier, wherein the otologically acceptable topical carrier is propylene glycol and, wherein the otologically acceptable topical carrier is present in an amount of about 50% to about 99.995% by weight of the liquid composition; and wherein the liquid composition is formulated for topical administration to the external ear canal.

4. A liquid composition for the treatment and/or prevention of excessive cerumen production or inhibiting production of cerumen comprising;
a) an active ingredient selected from the group consisting of muscarinic antagonists, muscarinic antagonist analogs, muscarinic antagonist derivatives, and combinations thereof;
wherein the active ingredient is present in a total amount of 0.005% to 15% by weight of the liquid composition;
b) an otologically acceptable topical carrier, wherein the otologically acceptable topical carrier is propylene glycol and, wherein the otologically acceptable topical carrier is present in an amount of about 50% to about 99.995% by weight of the liquid composition; and
wherein the liquid composition is formulated for topical administration to the external ear canal.

5. The liquid composition of claim 4 wherein the active ingredient is a natural muscarinic antagonist agent or pharmaceutically acceptable prodrug or salt thereof selected from the group consisting of atropine and scopolamine.

6. The liquid composition of claim 4 wherein the active ingredient is a derivative or analog of a natural muscarinic antagonist agent or pharmaceutically acceptable prodrug or salt thereof selected from the group consisting of homatropine, methscopolamine, ipratropium, and tiotropium.

7. The liquid composition of claim 4 wherein the active ingredient is scopolamine, methscopolamine, or a combination thereof.

8. A method of treating or preventing excessive cerumen in a subject in need thereof, comprising;
a) administering to the external ear canal liquid composition comprising;
(i) a compound or pharmaceutically acceptable prodrug or salt thereof as an active ingredient, wherein the compound or a combination thereof is selected from the group consisting of

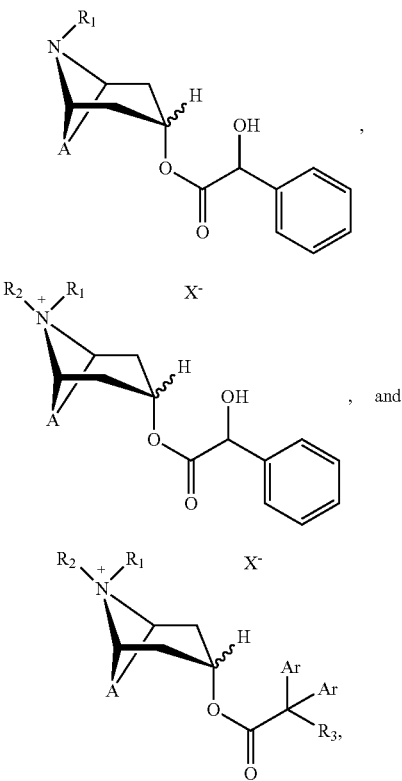

wherein A is a group selected from

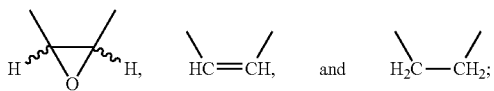

$R^1$ and $R^2$ are each independently hydrogen, $C_1$-$C_4$-alkyl optionally substituted with hydroxy or halogen;

$R^3$ is hydroxy, $C_1$-$C_4$-alkyl, $C_1$-$C_4$-alkoxy, $CF_3$, or fluorine;

$X^-$ denotes an anion selected from among chlorine, bromine, iodine, methanesulphonate or trifluoromethanesulphonate; and Ar is phenyl, naphthyl, thienyl, and furyl, each optionally mono- or disubstituted with one or two groups selected from $C_1$-$C_4$-alkyl, $C_1$-$C_4$-alkoxy, hydroxy, fluorine, chlorine, bromine, or $CF_3$;

wherein the compound is present in a total amount of 0.005% to 15% by weight of the liquid composition; and ii) an otologically acceptable topical carrier, wherein the otologically acceptable topical carrier is propylene glycol and wherein the otologically acceptable topical carrier is present in a total amount of about 50% to about 99.995% by weight of the liquid composition.

9. The method of claim 8 wherein the liquid composition is administered by spraying or by instillation, in the form of drops into the external ear canal.

10. The method of claim 8 wherein the liquid composition is administered by a suitable device for irrigation of the external ear canal.

11. The method of claim 8 wherein the liquid composition is administered at least once a day for at least 3 weeks.

12. The method of claim 8, further comprising;
a) selecting a subject in need of preventing excessive cerumen,
wherein the subject in need of preventing excessive cerumen is observed to have one or more signs, symptoms or complications of excessive human cerumen prior to administering the liquid composition;
b) instructing the selected subject to administer the liquid composition at least once a day for 3 weeks;
c) observing the selected subject for one or more signs, symptoms or complications of excessive human cerumen after administering the liquid composition for 3 weeks; and
d) instructing the selected subject to continue administering the liquid composition indefinitely if the one or more signs, symptoms or complications of excessive human cerumen observed in step a) is attenuated by at least 50% after administering the liquid composition for at least 3 weeks;
wherein the one or more signs, symptoms or complications of excessive human cerumen is selected from the group consisting of occlusion of the ear canal, discomfort, decreased hearing, itching, otic fullness, ringing in the ears, hearing aid issues, otitis externa, and tinnitus.

13. The method of claim 8, further comprising;
a) selecting a subject in need of treating excessive cerumen,
wherein the subject in need of treating excessive cerumen is observed to have one or more signs, symptoms or complications of excessive human cerumen prior to administering the liquid composition;
b) instructing the selected subject to administer the liquid composition at least once a day for 3 weeks;
c) observing the selected subject for one or more signs, symptoms or complications of excessive human cerumen after administering the liquid composition for 3 weeks; and
d) instructing the selected subject to continue administering the liquid composition for at least an additional 6 months if the one or more signs, symptoms or complications of excessive human cerumen observed in step a) is attenuated by at least 50% after administering the liquid composition for at least 3 weeks;
wherein the one or more signs, symptoms or complications of excessive human cerumen is selected from the group consisting of occlusion of the ear canal, discomfort, decreased hearing, itching, otic fullness, ringing in the ears, hearing aid issues, otitis externa, and tinnitus.

14. The method of claim 12 wherein at least one hearing aid issue is selected from the group comprising of auditory feedback from hearing aid, damage to hearing aid, and pain and/or discomfort with hearing aid use.

15. A method of preventing excessive cerumen, comprising;
   administering to the external ear canal liquid composition comprising a synthetic structural analog of atropine or pharmaceutically acceptable prodrug or salt thereof as an active ingredient, wherein the active ingredient is present in a total amount of 0.005% to 15% by weight of the liquid composition; and
   an otologically acceptable topical carrier, wherein the otologically acceptable topical carrier is propylene glycol and wherein the otologically acceptable topical carrier is present in an amount of about 50% to about 99.995% by weight of the liquid composition.

16. The method of claim 15 wherein the synthetic structural analog of atropine or pharmaceutically acceptable prodrug or salt thereof is selected from the group consisting of homatropine, methscopolamine, ipratropium, and tiotropium.

17. A method of preventing excessive cerumen, comprising;
   topically administering to the external ear canal liquid composition comprising an active ingredient methscopolamine, scopolamine, or its pharmaceutically acceptable prodrug or salt thereof, wherein the active ingredient is present in a total amount of 0.005% to 15% by weight of the liquid composition; and an otologically topical acceptable carrier wherein the otologically acceptable topical carrier is propylene glycol and wherein the otologically acceptable topical carrier is present in an amount of about 50% to about 99.995% by weight of the liquid composition for at least once a day for at least 3 weeks.

18. A method of preventing excessive cerumen buildup in a subject in need thereof, the method comprising;
   a) removing all cerumen within the external ear canal;
   b) topically administering to the external ear canal liquid composition comprising an active ingredient methscopolamine, scopolamine, or its pharmaceutically acceptable prodrug or salt thereof, wherein the active ingredient is present in a total amount of 0.005% to 15% by weight of the liquid composition; and an otologically acceptable topical carrier after cerumen within the external ear canal is removed wherein the otologically acceptable topical carrier is propylene glycol and wherein the otologically acceptable topical carrier is present in an amount of about 50% to about 99.995% by weight of the liquid composition; and
   c) continuing topical administration of the liquid composition to the external ear canal at least once a day.

19. The method of claim 18 wherein cerumen buildup is less than 50% after 3 weeks of at least once a day topical administration of the liquid composition to the external ear canal.

20. A liquid composition for the treatment and/or prevention of excessive cerumen, comprising;
   a compound or pharmaceutically acceptable prodrug or salt thereof, wherein the compound or a combination thereof is selected from the group consisting of

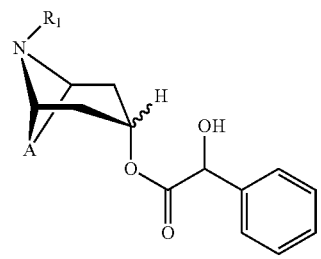

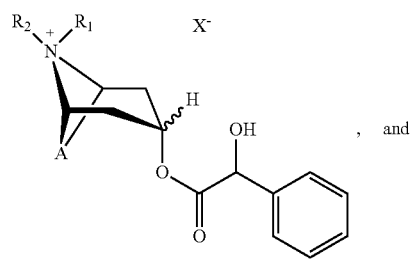

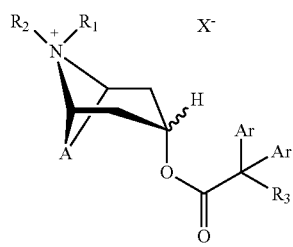

wherein A is a group selected from

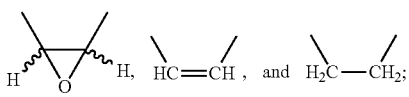

$R^1$ and $R^2$ are each independently hydrogen, $C_1$-$C_4$-alkyl optionally substituted with hydroxy or halogen;
$R^3$ is hydroxy, $C_1$-$C_4$-alkyl, $C_1$-$C_4$-alkoxy, $CF_3$, or fluorine;
$X^-$ denotes an anion selected from among chlorine, bromine, iodine, methanesulphonate or trifluoromethanesulphonate; and
Ar is phenyl, naphthyl, thienyl, and furyl, each optionally mono- or disubstituted with one or two groups selected from $C_1$-$C_4$-alkyl, $C_1$-$C_4$-alkoxy, hydroxy, fluorine, chlorine, bromine, or $CF_3$;
   wherein the compound is present in a total amount of 0.005% to 15% by weight of the liquid composition;
   an otologically acceptable topical carrier, wherein the otologically acceptable topical carrier is present in an amount of about 50% to about 99.995% by weight of the liquid composition;
   wherein the liquid composition is formulated for topical administration to the external ear canal; and
   wherein the liquid composition does not comprise triglycerides.

21. The liquid composition of any one of the claim 1 or 4, wherein the liquid composition prevents ear wax accumulation, hearing loss, or ear wax impactions caused by hearing aid use in a subject.

* * * * *